United States Patent [19]
Murray et al.

[11] Patent Number: 5,187,263
[45] Date of Patent: Feb. 16, 1993

[54] EXPRESSION OF BIOLOGICALLY ACTIVE PDGE ANALOGS IN EUCARYOTIC CELLS

[75] Inventors: Mark J. Murray; James D. Kelly, both of Seattle, Wash.

[73] Assignee: ZymoGenetics, Inc., Seattle, Wash.

[21] Appl. No.: 818,397

[22] Filed: Jan. 2, 1992

Related U.S. Application Data

[60] Continuation of Ser. No. 235,381, Aug. 22, 1988, abandoned, which is a division of Ser. No. 896,485, Aug. 13, 1986, Pat. No. 4,766,073, which is a continuation-in-part of Ser. No. 705,175, Feb. 25, 1985, Pat. No. 4,801,542, which is a continuation-in-part of Ser. No. 660,496, Oct. 12, 1984, Pat. No. 4,769,328.

[51] Int. Cl.$^5$ ............................................. C07K 13/00
[52] U.S. Cl. .................................... 530/399; 435/69.4
[58] Field of Search ................ 530/350, 399; 435/69.4

[56] References Cited

U.S. PATENT DOCUMENTS

| | | | |
|---|---|---|---|
| 4,350,687 | 9/1982 | Lipton et al. | 530/300 |
| 4,443,546 | 4/1984 | Stemerman et al. | 435/240 |
| 4,479,896 | 10/1984 | Antoniades | 530/399 |
| 4,546,082 | 10/1985 | Kurjan et al. | 435/172.3 |
| 4,568,640 | 2/1986 | Rubin | 435/70 |
| 4,588,585 | 5/1986 | Mark et al. | 424/85 |
| 4,590,003 | 5/1986 | Twardzik et al. | 530/330 |
| 4,599,311 | 7/1986 | Kawasaki | 435/71 |
| 4,605,413 | 8/1986 | Urry et al. | 623/11 |
| 4,645,828 | 2/1987 | Twardzik et al. | 530/324 |
| 4,673,640 | 6/1987 | Backman | 435/68 |

FOREIGN PATENT DOCUMENTS

| | | |
|---|---|---|
| 116201 | 10/1983 | European Pat. Off. |
| 103409 | 3/1984 | European Pat. Off. |
| 123294 | 10/1984 | European Pat. Off. |
| 123544 | 10/1984 | European Pat. Off. |
| WO85/04413 | 10/1985 | PCT Int'l Appl. |
| WO86/03122 | 6/1986 | PCT Int'l Appl. |
| 2137631 | 10/1984 | United Kingdom |
| 2146335 | 4/1985 | United Kingdom |

OTHER PUBLICATIONS

Collins et al. "Cultured human endothelial cells express PDGF B Chain:CDNA cloning & structural analysis", Nature 316: 748–750 (1985).

Waterfield et al. "PDGF is structurally related to the putative transforming protein p28$^{sis}$ of simian sarcoma virus" Nature 304: 35–39 (1983).

Poggi et al., "Partial Purificiation and Characterization of Porcine Platelet–derived Growth Factor (PDGF)," *Exp. Cell Res.* 150:436–441, 1984.

Stroobant et al., "Purification and Properties of Porcine Platelet-Derived Growth Factor," *EMBO J.* 12:2963–2967, 1984.

Wang et al., "A v-sis Oncogene Protein Produced in Bacteria Competes for Platelet–Derived Growth Factor Binding to Its Receptor," *J. Biol. Chem.* 259:10645–10648, 1984.

Antoniades, "Platelet–Derived Growth Factor and Malignant Transformation," *Biochem. Pharm.* 33:2823–2828, 1984.

(List continued on next page.)

*Primary Examiner*—David L. Lacey
*Assistant Examiner*—Shelly J. Guest
*Attorney, Agent, or Firm*—Seed and Berry

[57] ABSTRACT

Methods for expressing a variety of biologically active PDGF analogs in eucaryotic cells are disclosed. The methods generally comprise introducing into a eucaryotic host cell a DNA construct capable of directing the expression and secretion of biologically active PDGF analogs in eucaryotic cells. The DNA construct contains a transcriptional promoter followed downstream by a suitable DNA sequence. The DNA sequence may encode a protein substantially homologous to the A-chain or the B-chain of PDGF, or a portion thereof, or an A-B heterodimer. In addition, a portion of the DNA sequence may encode at least a portion of the A-chain, while another portion encodes at least a portion of the B-chain of PDGF. Eucaryotic cells transformed with these DNA constructs are also disclosed. Methods of promoting the growth of mammalian cells, comprising incubating the cells with a biologically active PDGF analog expressed by a eucaryotic host cell transformed with such a DNA construct, are also disclosed.

1 Claim, 11 Drawing Sheets

OTHER PUBLICATIONS

Deuel and Huang, "Platelet-derived Growth Factor," *J. Clin. Invest.* 74:669–676, 1984.

Huang et al., "Transforming Protein of Simian Sarcoma Virus Stimulates Autocrine Growth of SSV-Transformed Cells Through PDGF Cell-Surface Receptors," *Cell* 39:79–87, 1984.

Owen et al., "Simian Sarcoma Virus (SSV) Transformed Cells Secrete a Platelet-Derived Growth Factor (PDGF)-Like Mitogen," *Fed. Proc.* 43:373, 1984.

Owen et al., "Simian Sarcoma Virus-Transformed Cells Secrete a Mitogen Identical to Platelet-Derived Growth Factor," *Science* 225:54, 1984.

Robbins et al., "Structural and Immunological Similarities Between Simian Sarcoma Virus Gene Product(s) and Human Platelet-Derived Growth Factor," *Nature* 305:605–608, 1983.

Josephs et al., "Transforming Potential of Human C-sis Nucleotide Sequences Encoding Platelet Derived Growth Factor," *Science* 225:636–639, 1984.

Robbins et al., "Close Similarities between the Transforming Gene Product of Simian Sarcoma Virus and Human Platelet-derived Growth Factor", *Cancer Cells* 1:35–42, 1984.

Deuel et al., "Expression of a Platelet-Derived Growth Factor-Like Protein in Simian Sarcoma Virus Transformed Cells," *Science* 221:1348–1350.

Raines et al., "Biologic activity of platelet-derived growth factor-related sequences expressed in yeast," *J. Cell. Biochem. Supp.* (US) (9A):136 (1985).

Waterfield et al., "Platelet-derived growth factor is structurally related to the putative transforming protein p28sis of simian sarcoma virus", *Nature* 304:35–39, 1983.

Doolittle et al., "Simian Sarcoma Virus Onc Gene, V-sis Is Derived From the Gene (or Genes) Encoding a Platelet-Derived Growth Factor," *Science* 221:275–277, 1983.

Dicker et al., "Similarities Between Fibroblast-Derived Growth Factor and Platelet-Derived Growth Factor," *Exp. Cell Res.* 135:221–227, 1981.

Dicker et al., "Similarities between fibroblast-derived growth factor and platelet-derived growth factor," *Chem. Abstr.* 95:201393r, 1981.

Heldin et al., "Platelet-derived growth factor," *Biochem. J.* 193:907–913, 1981.

Robbins et al., "In Vivo Identification of the Transforming Gene Product of Simian Sarcoma Virus," *Science* 218:1131–1133, 1982.

Devare et al., "Nucleotide sequence of the simian sarcoma virus genome Demonstration that its acquired cellular sequences encode the transforming gene product p28$^{sis}$," *Proc. Natl. Acad. Sci. USA* 80:731–735, 1983.

Devare et al., "Expression of the PDGF-Related Transforming Protein of Simian Sarcoma Virus in *E. coli*," *Cell* 36:43–49, 1984.

Deuel et al., "Human Platelet-Derived Growth Factor," *J. Biol. Chem.* 256:8896–8899, 1981.

Johnsson et al., "The c-sis gene encodes a precursor of the B chain of platelet-derived growth factor", *Chem. Abstr.* 101:84809k, 1984.

Bourne and Rozengurt, "An 18,000 Molecular Weight Polypeptide Induces Early Events and Stimulates DNA Synthesis in Cultured Cells", *Proc. Natl. Acad. Sci. USA* 73:4555–4559, 1976.

Waterfield et al., "Relationship between the Transforming Protein of Simian Sarcoma Virus and Human Platelet-derived Growth Factor", *Cancer Cells* 1:25–33, 1984.

Heldin et al., "Mechanism of action of platelet-derived growth factor and its relation to oncogenes," *J. Embryol. Exp. Morphol.* 82 Suppl:41, 1984.

Robson et al., "Predictions of the conformation and antigenic determinants of the v-sis viral oncogene product homologous with human platelet-derived growth factor," *Chem. Abstr.* 102:164950k, 1985.

Johnsson et al., "Platelet-derived growth factor agonist activity of a secreted form of the v-sis oncogene product," *Proc. Natl. Acad. Sci. USA* 82:1721–1725, 1985.

Gazit et al., "Expression of the Normal Human sis/PDGF-2 Coding Sequence Induces Cellular Transformation," *Cell* 39:89–97, 1984.

Johnsson et al., "The Structural Relationship Between Human Platelet-Derived Growth Factor and the Transforming Protein of Simian Sarcoma Virus," *J. Cell Biochem. Suppl.* 8A:64, 1984.

Nister et al., "A Platelet-Derived Growth Factor Analog Produced by a Human Clonal Glioma Cell Line," *Ann. NY Acad. Sci.* 397:25–33, 1982.

(List continued on next page.)

OTHER PUBLICATIONS

Rozengurt et al., "Inhibition of Epidermal Growth Factor Binding to Mouse Cultured Cells by Fibroblast-derived Growth Factor", *J. Biol. Chem.* 257:3680–3686, 1982.

Nister et al., "A glioma-derived analog to platelet-derived growth factor: Demonstration of receptor competing activity and immunological crossreactivity," *Proc. Natl. Acad. Sci. USA* 81:926–930, 1984.

Antoniades and Hunkapiller, "Human Platelet-Derived Growth Factor (PDGF): Amino-Terminal Amino Acid Sequence," *Science* 220:963–965, 1983.

Antoniades, "Human Platelet-Derived Growth Factor (PDGF): Purification of PDGF-I and PDGF-II and Separation of Their Reduced Subunits," *Proc. Natl. Acad. Sci. USA* 78:7314–7317, 1981.

Johnsson et al., "Platelet-Derived Growth Factor: Identification of Constituent Polypeptide Chains," *Biochem. Biophys. Res. Comm.* 104:66–74, 1982.

Bowen-Pope et al., "Production of Platelet-Derived Growth Factor-Like Molecules and Reduced Expression of Platelet-Derived Growth Factor Receptors Accompany Transformation by a Wide Spectrum of Agents," *Proc. Natl. Acad. Sci. USA* 81:2396–2400, 1984.

Scher et al., "Transforming Viruses Directly Reduce the Cellular Growth Requirement for a Platelet Derived Growth Factor," *J. Cell Physiol*, 97:371–380, 1978.

Chesterman et al., "Comparison of Platelet-Derived Growth Factor Prepared From Release Products of Fresh Platelets and From Outdated Platelet Concentrates," *Biochem. Biophys. Res. Comm.* 116:809–816, 1983.

Westermark et al., "Platelet-Derived Growth Factor," *Horm. Cell Reg.* 8:9–15, 1984.

Niman, "Antisera to a synthetic peptide of the sis viral oncogene product recognize human platelet-derived growth factor," *Nature* 307:180–183, 1984.

Barth et al., "Structure and Expression of Platelet-Derived Growth Factor/c-sis Gene," *J. Cell Biochem. Suppl.* 8A:66, 1984.

Wang et al., "Interaction of the V-SIS Gene Product With PDGF Receptor," *J. Cell Biochem. Suppl.* 8A:258, 1984.

Goustin et al., "Expression of c-sis Oncogene and PDGF Receptors in Cell Lines Derived From Hydatidiform Mole: Implications for Autocrine Growth Control," *J. Cell Biol.* 99(4 part 2):149a, 1984.

Hannink and Donoghue, "Requirement for a Signal Sequence in Biological Expression of the v-sis Oncogene," *Science* 226: 1197–1199, 1984.

Niman et al., "Detection of High Molecular Weight Forms of Platelet-Derived Growth Factor by Sequence-Specific Antisera," *Science* 226:701–703, 1984.

Fors et al., "Structural and Functional Studies on the Genes Encoding Platelet-Derived Growth Factor and the Platelet-Derived Growth Factor Receptor," *J. Cell Biochem.* 0 (8 part 1):254, 1984.

Raines and Ross, "Platelet-Derived Growth Factor," *J. Biol. Chem.* 257:5154–5160, 1982.

Devare et al., "Nucleotide sequence of the transforming gene of simian sarcoma virus," *Proc. Natl. Acad. Sci. USA* 79:3179–3182, 1982.

Francis et al., "Chronic Myeloid Leukaemia and the Philadelphia Translocation: Do the C-SIS Oncogene and Platelet-Derived Growth Factor Provide the Link?" *Leuk. Res.* 7:817–820, 1983.

Bowen-Pope et al., "The Ability of Cells to Synthesize and Respond to Platelet-Derived Growth Factor: Possible Involvement in Several Forms of Growth Regulation," *J. Cell Biochem. Suppl.* 8B:94, 1984.

Chiu et al., "Nucleotide Sequence Analysis Identifies the Human c-sis Proto-Oncogene as a Structural Gene for Platelet-Derived Growth Factor," *Cell* 37:123–129, 1984.

Antoniades et al., "Purification of human platelet-derived growth factor," *Chem. Abstr.* 91:15439c, 1979.

Antoniades et al., "Purification of human platelet-derived growth factor," *Proc. Natl. Acad. Sci. USA* 76: 1809–1813, 1979.

Graves et al., "Detection of c-sis Transcripts and Synthesis of PDGF-Like Proteins by Human Osteosarcoma Cells," *Science* 226:972–974, 1984.

Heldin et al., "Chemical and Biological Properties of a Growth Factor From Human-Cultured Osteosarcoma Cells: Resemblance With Platelet-Derived Growth Factor," *J. Cell Physiol.* 105: 235–246, 1980.

Betsholtz et al., "Coexpression of a PDGF-Like Growth Factor and PDGF Receptors in a Human Osteosarcoma Cell Line: Implications for Autocrine Recep- (List continued on next page.)

OTHER PUBLICATIONS tor Activation," *Cell* 39:447–457, 1984.

Graves et al., "High Molecular Weight Precursors to Platelet-Derived Growth Factor (PDGF) are Synthesized by Human Osteosarcoma Cells," *Fed. Proc.* 43:373, 1984.

Antoniades et al., "Purification and Properties of the Human Platelet-Derived Growth Factor," *Fed. Proc.* 38 (3 part 1):634, 1979.

Ross et al., "The Platelet-Derived Growth Factor," *J. Supramol. Struct.* 8 (suppl. 3):175, 1979.

Wasteson et al., "Chemical and Biological Properties of Platelet Derived Growth Factor," *J. Supramol. Struct.* 9 (suppl. 4):205, 1980.

Josephs et al., "5′ Viral and Human Cellular Sequences Corresponding to the Transforming Gene of Simian Sarcoma Virus," *Science* 219:503–505, 1983.

Heldin et al., "Platelet-derived growth factor: Purification and partial characterization," *Proc. Natl. Acad. Sci. USA* 76:3722–3726, 1979.

Huang et al., "Human Platelet-Derived Growth Factor: Purification and Initial Characterization," in *Differentiation and Hematopoietic Cell Surfaces*, 225–230, 1982. Alan R. Liss, Inc., N.Y.

Davis and Tai, "The Mechanism of Protein Secretion Across Membranes," *Nature* 283:433–438, 1980.

Favera et al., "A human onc gene homologous to the transforming gene (v-sis) of simian sarcoma virus," *Nature* 292:31–35, 1981.

Wong-Staal and Gallo, "The Transforming Genes of Primate and Other Retroviruses and Their Human Homologs," *Adv. Vir. Oncol.* 1:153–171, 1982.

Betsholtz et al., "Synthesis of a PDGF-Like Growth Factor in Human Glioma and Sarcoma Cells Suggests the Expression of the Cellular Homologue to the Transforming Protein of Simian Sarcoma Virus", *Biochem. Biophys. Res. Comm.* 117:176–182, 1983.

Thiel and Hafenrichter, "Simian Sarcoma Virus Transformation-Specific Glycopeptide: Immunological Relationship to Human Platelet-Derived Growth Factor," *Virol.* 136:414–424, 1984.

Seifert et al., "Developmentally regulated production of platelet-derived growth factor-like molecules," *Nature* 311:669–671, 1984.

Seifert et al., "Developmentally regulated production platelet-derived growth factor-like molecules," *J. Cell Biochem.* 0 (8 part 1):257, 1984.

Rizzino and Bowen-Pope, "Production of and Response to PDGF-Like Factors by Early Embryonic Cells," *Fed. Proc.* 43:373, 1984.

Alber and Kawasaki, "Nucleotide Sequence of the Triose Phosphate Isomerase Gene of *Saccharomyces cerevisiae*," *J. Molec. Appl. Genet.* 1:419–434, 1982.

Kurjan et al., "Structure of a Yeast Pheromone Gene (MFa): A Putative a-Factor Precursor Contains Four Tandem Copies of Mature a-Factor," *Cell* 30:933–943, 1982.

Brake et al., "a-Factor-Directed Synthesis and Secretion of Mature Foreign Proteins in *Saccharomyces cerevisiae*," *Proc. Natl. Acad. Sci. USA* 81:4642–4646, 1984.

Bitter et al., "Secretion of Foreign Proteins from *Saccharomyces cerevisiae* Directed by Alpha Factor Gene Fusions," *Proc. Natl. Acad. Sci. USA* 81:5330–5334, 1984.

Woo et al., "Differential phosphorylation of the progesterone receptor by insulin, epidermal growth factor, and platelet-derived growth factor receptor tyrosine protein kinases," *Chem. Abstr.* 104: 45883x, 1986.

Eva et al., "Cellular genes analogous to retroviral onc genes are transcribed in human tumour cells," *Nature* 295:116–119.

Wong-Staal et al., "The v-sis transforming gene of simian sarcoma virus is a new onc gene of primate origin," *Nature* 294:273–275, 1981.

Edens et al., "Synthesis and Processing of the Plant Protein Thaumatin in Yeast," *Cell* 37:629, 1984.

Wasteson et al., "The Platelet-Derived Growth Factor: Structural and functional Aspects," *Thromb. Hemostas.* 50(1):87, 1983.

FIG. 1A

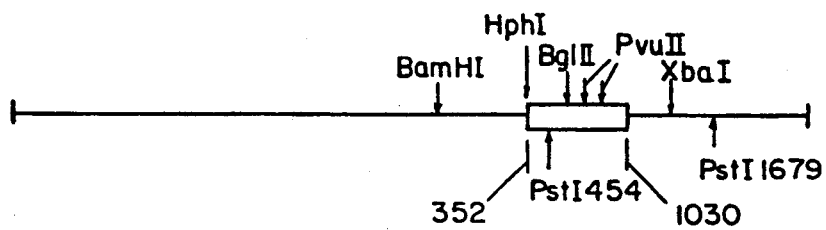

FIG. 1B

```
Hph I                    v-sis-helper viral junction
 |        367            |        382                     397
CT'ATG ACC CTC ACC TGG CAG GGG GAC CCC ATT CCT GAG GAG CTC TAT AAG ATG
   MET Thr Leu Thr Trp Gln Gly Asp Pro Ile Pro Glu Glu Leu Tyr Lys MET

|Pst I
          412                 427                 442        |  457
CTG AGT GGC CAC TCG ATT CGC TCC TTC AAT GAC CTC CAG CGC CTG CTG CAG GGA
Leu Ser Gly His Ser Ile Arg Ser Phe Asn Asp Leu Gln Arg Leu Leu Gln Gly 472                 487                 502
GAG TCC GGA AAA GAA GAT GGG GCT GAG CTG GAC CTG AAC ATG ACC CGC TCC CAT
Asp Ser Gly Lys Glu Asp Gly Ala Glu Leu Asp Leu Asn MET Thr Arg Ser His 517                 532                 547                 562
TCT GGT GGC GAG CTG GAG AGC TTG GCT CGT GGG AAA AGG AGC CTG GGT TCC CTG
Ser Gly Gly Glu Leu Glu Ser Leu Ala Arg Gly Lys Arg Ser Leu Gly Ser Leu 577                 592                 607
AGC GTT GCC GAG CCA GCC ATG ATT GCC GAG TGC AAG ACA CGA ACC GAG GTG TTC
Ser Val Ala Glu Pro Ala MET Ile Ala Glu Cys Lys Thr Arg Thr Glu Val Phe

Bgl II
 622              637                 652                 667
GAG ATC TCC CGG CGC CTC ATC GAC CGC ACC AAT GCC AAC TTC CTG GTG TGG CCG
Glu Ile Ser Arg Arg Leu Ile Asp Arg Thr Asn Ala Asn Phe Leu Val Trp Pro
```

```
     682                    697                    712                    727
CCC TGC GTG GAG GTG CAG CGC TGC TCC GGC TGT TGC AAC AAC CGC AAC GTG CAG
Pro Cys Val Glu Val Gln Arg Cys Ser Gly Cys Cys Asn Asn Arg Asn Val Gln

|Pvu II
                 742         ↓      757                    772
TGC CGG CCC ACC CAA GTG CAG CTG CGG CCA GTC CAG GTG AGA AAG ATC GAG ATT
Cys Arg Pro Thr Gln Val Gln Leu Arg Pro Val Gln Val Arg Lys Ile Glu Ile 787                    802                    817                    832
GTG CGG AAG AAG CCA ATC TTT AAG AAG GCC ACG GTG ACG CTG GAG GAC CAC CTG
Val Arg Lys Lys Pro Ile Phe Lys Lys Ala Thr Val Thr Leu Glu Asp His Leu

Pvu II
         847                 862                    877
GCA TGC AAG TGT GAG ATA GTG GCA GCT GCA CGG GCT GTG ACC CGA AGC CCG GGG
Ala Cys Lys Cys Glu Ile Val Ala Ala Ala Arg Ala Val Thr Arg Ser Pro Gly 892                    907                    922                    937
ACT TCC CAG GAG CAG CGA GCC AAA ACG ACC CAA AGT CGG GTG ACC ATC CGG ACG
Thr Ser Gln Glu Gln Arg Ala Lys Thr Thr Gln Ser Arg Val Thr Ile Arg Thr 952                    967                    982                997
GTG CGA GTC CGC CGG CCC CCC AAG GGC AAG CAC CGG AAA TGC AAG CAC ACG CAT
Val Arg Val Arg Arg Pro Pro Lys Gly Lys His Arg Lys Cys Lys His Thr His 1012                   1027                 1043       1053
GAC AAG ACG GCA CTG AAG GAG ACC CTC GGA GCC TAA GGGCATCGGC AGGAGAATAT
Asp Lys Thr Ala Leu Lys Glu Thr Leu Gly Ala 1063       1073       1083       1093       1103       1113       1123
GGGCAGCGGG TCTCCTGCCA GCGGCCTCCA GCATCTTGCC CAGCAGCTCA AGAAGAGAAA AAAGGACTGA 1133       1143       1153       1163       1173       1183       1193
ACTCCACCAC CATCTTCTTC CCTTAACTCC AAAAACTTGA AATAAGAGTG TGAAAGAGAC TGATAGGGTC 1203       1213       1223       1233       1243       1253       1263
GCTGTTTGAA AAAAACTGGC TCCTTCCTCT GCACCTGGCC TGGGCCACAC CCAAGTGCTG TGGACTGGCC 1273       1283       1293       1303       1313       1323       1333
CGAGGGGCCC TGCACGTGGC CCTGAGCACC TCTCAGTGTA GCCTGCCTGG TCCCTAGACC CCTGGCCAGC

XbaI| v-sis-helper viral junction
         1343       1353       1363       1373       ↓↓
TCCAAGGGGA GGCACCTCCA GGCAGGCCAG GCTACCTCGG GGGTCTAG
```

```
B CHAIN
   1                                           10              20      BglII    30
  →S L G S L T I A E P A M I A E C K T R T E V F E I S R R L I D R T N
                   S I E E A V P A V C K T R T V I Y E I P R S Q V D P T S
A CHAIN
   1                        10              20              25
  35 BstXI  40                                                        70
  A N F L V W P P C V E V Q R C S G C C N N R N V Q C R P T Q V Q L R P M Q V
  A N F L I W P P C V E V K R C T G C C N T S S V K C Q P S R V H H R S V K V
  30              40         50              60              70
                                                                  SphI  100          109
  R K I E I V R K K P I F K K A T V T L E D H L A C K C E T V A A A R P V T
  A K V E Y V R K K P K L K E V Q V R L E E H L E C A C A T T S L N P D Y R E
  70              80              90              100          104
```

EXPRESSION OF BIOLOGICALLY ACTIVE PDGE ANALOGS IN EUCARYOTIC CELLS

CROSS-REFERENCE TO RELATED APPLICATIONS

This application is a continuation of Ser. No. 07/235381, now abandoned, which is a divisional of Ser. No. 06/896485, now U.S. Pat. No. 4,766,073, which is a continuation-in-part of Ser. No. 06/705105, now U.S. Pat. No. 4,801,542, which is a continuation-in-part of Ser. No. 06/660496, now U.S. Pat. No. 4,769,328.

TECHNICAL FIELD

The present invention relates to the production of PDGF analogs in general, and more specifically, to the expression of biologically active PDGF analogs in eucaryotes.

BACKGROUND ART

Human platelet-derived growth factor (PDGF) has been shown to be the major mitogenic protein in serum for mesenchymal derived cells. This is well documented by numerous studies of platelet extracts or purified PDGF induction of either cell multiplication or DNA synthesis (a prerequisite for cell division) in cultured smooth muscle cells, fibroblasts and glial cells (Ross et al., PNAS 71: 1207, 1974; Kohler and Lipton, *Exp. Cell Res.* 87: 297, 1974; Westermark and Wasteson, *Exp. Cell Res.* 98: 170, 1976; Heldin et al., *J. Cell Physiol.* 105: 235, 1980; Raines and Ross, *J. Biol. Chem.* 257: 5154, 1982). Furthermore, PDGF is a potent chemoattractant for cells that are responsive to it as a mitogen (Grotendorst et al., *J. Cell Physiol.* 113: 261, 1982; Seppa et al., *J. Cell Biol.* 92: 584, 1982). It is not generally the case that mitogens also act as chemotactic agents. Due to its mitogenic activity, PDGF is useful as an important component of a defined medium for the growth of mammalian cells in culture, making it a valuable research reagent with multiple applications in the study of animal cell biology.

In vivo, PDGF normally circulates stored in the alpha granules of platelets. Injury to arterial endothelial linings causes platelets to adhere to the exposed connective tissue and release their granules. The released PDGF is thought to chemotactically attract fibroblasts and smooth muscle cells to the site of injury and to induce their focal proliferation as part of the process of wound repair (Ross and Glomset, *N. Eng. J. of Med.* 295: 369, 1976).

It has been postulated that as a part of this response to injury, PDGF released by platelets may play a causative role in the development of the proliferative lesions of atherosclerosis (Ross and Glomset, ibid.) which is one of the principal causes of myocardial and cerebral infarction. Strategies for the prophylaxis and treatment of atherogenesis in the past have been narrowly directed toward reducing risk factors for the disease, such as lowering blood pressure in hypertensive subjects and reducing elevated cholesterol levels in hypercholesterolemic subjects.

Recent studies have shown that at least one of the two protein chains comprising PDGF and the putative transforming protein of simian sarcoma virus (SSV), an acute transforming retrovirus, appear to have arisen from the same or closely related cellular genes. In particular, computer analysis of a partial amino acid sequence of PDGF has revealed extensive homology with the gene product, $p28^{sis}$, of SSV (Doolittle et al., *Science* 221: 275, 1983; Waterfield et al., *Nature* 304: 35, 1984; and Johnson et al., *EMBO* 3: 921, 1984). Further, more recent studies have illustrated that $p28^{sis}$ and PDGF show antigenic as well as structural similarities (Robbins et al., *Nature* 305: 605, 1983; Niman, *Nature* 307: 180, 1984).

Although previous attempts, such as that summarized in Devare et al. (*Cell* 36: 43, 1984), have been made to express the v-sis gene in a transformed microorganism, they have not been successful in producing mitogenic material. More recently, investigators have described the production of $p28^{sis}$ in E. coli as a fusion protein (Wang et al., *J. Biol. Chem.* 259: 10645, 1984). This protein appears to compete with PDGF for binding to PDGF receptor sites. While SSV transformed rodent cells have been shown to exhibit a mitogenic activity similar to PDGF (Deuel et al., *Science* 221: 1348, 1983; Owen et al., *Science* 225: 54, 1984), it is not clear that this activity is due to a gene product from SSV (i.e., $p28^{sis}$). Furthermore, cells transformed by a variety of viruses other than SSV produce a PDGF-like mitogen into the culture medium (Bowen-Pope et al., *PNAS* 81: 2396, 1984).

While natural PDGF may be isolated from human plasma or platelets as starting material, it is a complex and expensive process, in part due to the limited availability of the starting material. In addition, it is difficult to purify PDGF with high yield from other serum components due to its extremely low abundance and biochemical properties. Furthermore, the therapeutic use of products derived from human blood carries the risk of disease transmission due to contamination by, for example, hepatitis virus, cytomegalovirus, or the causative agent of Acquired Immune Deficiency Syndrome (AIDS).

In view of PDGF's clinical applicability in the treatment of injuries in which healing requires the proliferation of fibroblasts or smooth muscle cells and its value as an important component of a defined medium for the growth of mammalian cells in culture, the production of useful quantities of protein molecules similar to authentic PDGF which possess mitogenic activity is clearly invaluable.

In addition, the ability to produce relatively large amounts of PDGF or PDGF analogs would be a useful tool for elucidating the putative role of the v-sis protein, $p28^{sis}$, in the neoplastic process.

Further, since local accumulation of smooth muscle cells in the intamal layer of an arterial wall is central to the development of atherosclerotic lesions (Ross and Glomset, ibid.), one strategy for the prophylaxis and treatment of atherosclerosis would be to suppress smooth muscle cell proliferation. The ability to produce large amounts of PDGF would be useful in developing inhibitors or designing specific approaches which prevent or interfere with the in vivo activity of PDGF in individuals with atherosclerosis.

DISCLOSURE OF THE INVENTION

Briefly stated, the present invention discloses methods for expressing a variety of biologically active PDGF analogs in eucaryotic cells. In general, the methods comprise introducing into a eucaryotic host cell a DNA construct capable of directing the expression and secretion of biologically active PDGF analogs in eucaryotic cells. The DNA construct contains a transcriptional promoter followed downstream by an appropriate DNA sequence.

In one aspect of the present invention, the DNA sequence encodes a protein which is substantially homologous to the A-chain of PDGF. In another aspect of the present invention, the DNA sequence encodes a protein which is substantially homologous to the B-chain of PDGF. Within a third aspect of the present invention, a portion of the DNA sequence encodes a protein which is substantially homologous to at least a portion of the A-chain of PDGF, and another portion of said DNA sequence encodes a protein which is substantially homologous to at least a portion of the B-chain of PDGF, these portions of the DNA sequence encoding a protein having substantially the same biological activity as PDGF. In yet another aspect of the present invention, the DNA construct contains transcriptional promoters followed downstream by DNA sequences encoding polypeptide chains substantially homologous to the A- and B-chains of PDGF, the chains forming a heterodimer. The protein products produced by the methods utilizing these and other DNA sequences are also disclosed.

The present invention also discloses a variety of DNA constructs capable of directing the expression and secretion of biologically active PDGF analogs in eucaryotic cells. The DNA constructs contain a transcriptional promoter followed downstream by a suitable DNA sequence. As noted above, suitable DNA sequences include those encoding a protein which is substantially homologous to the A-chain or B-chain of PDGF. In addition, the DNA sequence may include a portion which is substantially homologous to at least a portion of the A-chain of PDGF, and a portion encoding a protein which is substantially homologous to at least a portion of the B-chain of PDGF. Further, the DNA construct may contain transcriptional promoters followed downstream by DNA sequences encoding polypeptide chains substantially homologous to the A- and B-chains of PDGF, the chains forming a heterodimer.

Eucaryotic host cells transformed with DNA constructs, such as those described above, are also disclosed. A preferred eucaryotic host cell in this regard is a yeast cell.

Another aspect of the present invention discloses methods of promoting the growth of mammalian cells, comprising incubating the cells with a biologically active PDGF analog expressed by a eucaryotic host cell transformed with a DNA construct as described above, and a signal sequence capable of directing the secretion of the protein from the eucaryotic cell.

Other aspects of the invention will become evident upon reference to the following detailed description and attached drawings.

BRIEF DESCRIPTION OF THE DRAWINGS

FIG. 1A is a schematic restriction map of the proviral genome of SSV.

FIG. 1B depicts the nucleotide sequence and predicted amino acid sequence encoded by the v-sis region of the SSV genome.

FIG. 9 depicts the amino acid sequences of the mature A- and B-chains of PDGF.

BEST MODE FOR CARRYING OUT THE INVENTION

Figure 2:
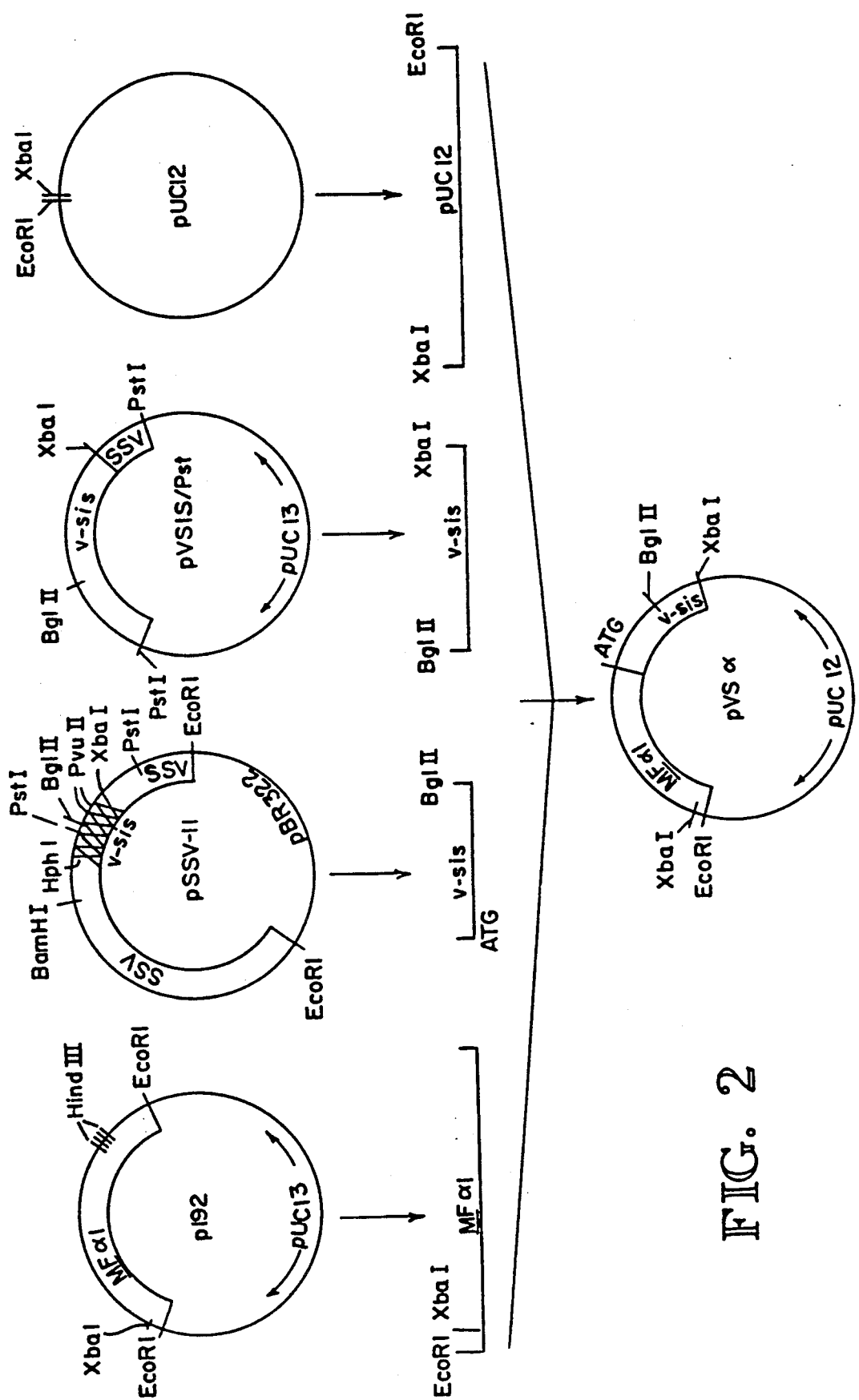
FIG. 2 illustrates the construction of a plasmid which contains the MFα1 promoter and secretory signal sequence upstream of the v-sis gene.

Prior to setting forth the invention, it may be helpful to an understanding thereof to set forth definitions of certain terms to be used hereinafter.

Polypeptide: A polymer of amino acids.

Reading Frame: The arrangement of nucleotide codons which encode an uninterrupted stretch of amino acids. During translation of an mRNA, the proper reading frame must be maintained. For example, the sequence GCUGGUUGUAAG may be translated into three reading frames or phases, depending on whether one starts with G, with C, or with U, and thus may yield three different peptide products. Translation of the template begins with an AUG codon, continues with codons for specific amino acids, and terminates with one of the translation termination codons.

Coding Sequence: DNA sequences which in the appropriate reading frame directly code for the amino acids of a protein.

Complementary DNA: or cDNA. A DNA molecule or sequence which has been enzymatically synthesized from the sequences present in an mRNA template.

Secretory Signal Sequence: That portion of a gene or cDNA encoding a signal peptide. A signal peptide is the amino acid sequence in a secretory protein which signals its translocation into the secretory pathway of the cell. Signal peptides generally occur at the beginning (amino terminus) of the protein and are 20-40 amino acids long with a stretch of 9-10 hydrophobic amino acids in their center. Very often the signal sequence is proteolytically cleaved from the protein during the process of secretion.

Cell Surface Receptor: A protein molecule at the surface of a cell which specifically interacts with or binds a molecule approaching the cell's surface. Once the receptor has bound the cognate molecule, it effects specific changes in the physiology of the cell.

Mitogen: A molecule which stimulates cells to undergo mitosis. Mitosis is asexual somatic cell division leading to two daughter cells, each having the same number of chromosomes as the parent cell.

Transformation: The process of stably and hereditably altering the genotype of a recipient cell or microorganism by the introduction of purified DNA. This is typically detected by a change in the phenotype of the recipient organism.

Transcription: The process of producing a mRNA template from a structural gene.

Expression: The process, starting with a structural gene or cDNA, of producing its polypeptide, being a combination of transcription and translation. An expression vector is a plasmid-derived construction designed to enable the expression of a gene or cDNA carried on the vector.

Plasmid: An extrachromosomal, double-stranded DNA sequence comprising an intact "replicon" such that the plasmid is replicated in a host cell. When the plasmid is placed within a unicellular organism, the characteristics of that organism may be changed or transformed as a result of the expression of the DNA sequences of the plasmid. For example, a plasmid carrying the gene for tetracycline resistance ($tet^R$) transforms a cell previously sensitive to tetracycline into one which is resistant to it.

Yeast Promoter: DNA sequences upstream from a yeast gene which promote its transcription.

Biological Activity: Some function or set of activities performed by a molecule in a biological context (i.e., in an organism or an in vitro facsimile). The hallmark of PDGF biological activity is the induction of DNA synthesis and mitogenesis following the binding of PDGF to its specific cell surface receptor on responsive cell types. Other biological effects of human platelet PDGF may include: directed cell migration (chemotaxis) and cell activation; phospholipase activation; increased phosphatidylinositol turnover and prostaglandin metabolism; stimulation of both collagen and collagenase synthesis by responsive cells; an indirect proliferative response of cells lacking PDGF receptors; and potent vasoconstrictor activity.

PDGF Analog: A polypeptide which is substantially homologous to at least a portion of the A-chain or the B-chain of PDGF, or both, wherein the polypeptide exhibits biological activity as defined herein.

As noted above, human platelet-derived growth factor (PDGF) has been shown to be a major mitogen in serum. PDGF is known to be composed of two polypeptide chains, an A-chain and a B-chain, which are held together by disulfide bonds to form the biologically active molecule. Following complete chemical reduction, the single polypeptide chains alone do not appear to exhibit any mitogenic activity (Raines and Ross, ibid.), and attempts to reconstitute activity by reoxidation of the reduced polypeptides have not been successful. Recently, the amino acid sequence of the B-chain has been determined and shown to be substantially homologous to a portion of the v-sis gene product, p28$^{sis}$ (Doolittle et al., ibid.; Waterfield et al., ibid.; and Johnson et al., ibid.). The homology between these two proteins strongly suggests that they are derived from the same or closely related cellular genes.

Given the fact that a single reduced B-chain polypeptide is not biologically active and that previous attempts directed toward expressing v-sis sequences in *E. coli* did not yield mitogenic material, it would not be expected that merely expressing a portion of the v-sis gene homologous to a portion of the PDGF gene in a microorganism would result in a molecule which exhibited mitogenic activity. The present invention, however, unlike the previous attempts noted above, was designed to express DNA sequences encoding PDGF A-chain or B-chain, as well as variants or derivatives of the A- and B-chains, such that the expressed molecules exhibit biological activity characteristic of PDGF. Further, the expression system of the present invention was designed to produce the gene product via a eucaryotic secretory pathway. This enables the expressed polypeptide molecules to be properly processed and places them in a cellular environment which allows them to be correctly folded and assembled. Indeed, the present invention, in contrast to previous efforts, results in the secretion of PDGF analogs which are biologically active.

In its biologically active form, PDGF is a heat-stable protein composed of heterogeneously sized species ranging between 28,000 and 31,000 Daltons, all of the individual species being active in stimulating DNA synthesis (Raines and Ross, ibid.; Deuel et al., *J. Biol. Chem.* 256: 8896, 1981; Antoniades, PNAS 78: 7314, 1981). Where individual species with molecular sizes of 27,000; 28,500; 29,000; and 31,000 Daltons have been isolated and analyzed, they show extensive tryptic peptide homology and have been found to have comparable mitogenic activity and amino acid composition (Raines and Ross, ibid.) The slight variations in size among the species are most probably due to differences in carbohydrate composition and minor proteolysis.

Through studies of PDGF which has been extensively purified from platelet-rich human plasma, it is likely, as noted above, that PDGF is composed of two polypeptide chains, an A-chain (14,000 Daltons) and a B-chain (16,000 Daltons), which are disulfide bonded together to form the biologically active dimer molecule (Raines and Ross; Deuel et al.; Antoniades, ibid.). The PDGF nomenclature found in the literature is not consistent (Doolittle et al.; Waterfield et al.; Raines and Ross; Johnsson et al., ibid.). The nomenclature of Johnsson et al. (ibid.), wherein the two polypeptides found in pure PDGF are called "A-chain" and "B-chain," is adopted. The B-chain is homologous to p28$^{sis}$ and was previously called "peptide I" (Waterfield et al., ibid.) or "1a" (Doolittle et al., ibid.). The A-chain was previously termed "peptide II" (Waterfield et al., ibid.) or "2a" (Doolittle et al., ibid.). Data derived from a partial amino acid sequence of PDGF indicate that the two polypeptide chains (A-chain and B-chain) show extensive homology (Doolittle et al., ibid.; Waterfield et al., ibid.; and Johnsson et al., ibid.; Antoniades and Hunkapiller, *Science* 220: 963, 1983). More specifically, it has been reported that there is 56% amino acid identity between the two chains. In addition, as shown in FIG. 9, there are several blocks of perfect homology between the two chains. Further, both of the chains contain eight cysteine residues at identical positions, suggesting that each polypeptide folds into a similar three-dimensional structure.

It appears that these two polypeptides are closely related members of a small family. The blocks of perfect homology between the A- and B-chains reflect regions of the protein which may be critical for function, while the less homologous regions may reflect portions of the protein which are less critical to its function. Therefore, as further exemplified by the present invention, certain portions of either the A- or B-chains may be deleted, while retaining biological activity within the resultant protein.

Based upon the teachings of the present invention, the homology between the A- and B-chains, together with the coincidence of cysteine residues, allows one skilled in the art to design additional suitable members of this homologous family. For example, one skilled in the art could construct a variety of hybrids between the A- and B-chain genes which would encode proteins in which the homologous domain structures were preserved. It is demonstrated herein that these proteins can be expected to assume a three-dimensional structure similar to wild-type A- or B-chains and retain biological activity.

The v-sis gene, as mentioned above, is the transforming gene of simian sarcoma virus (SSV). The v-sis gene has been cloned and its DNA sequence determined (Devare et al., *PNAS* 79: 3179, 1982; Devare et al., *PNAS* 80: 731, 1983). Analysis of this sequence revealed an open reading frame which could encode a 28,000 Dalton protein, designated p28$^{sis}$. Subsequently, such a protein was immunologically identified in SSV infected cells (Niman, ibid.; Robbins, ibid.). The predicted amino acid sequence of the v-sis gene product, p28$^{sis}$, was found to have a high degree of homology with the actual amino acid sequence of a portion of the B-chain of PDGF (Johnsson, ibid.). The homology of the PDGF B-chain to the v-sis gene product begins at amino acid 67 of p28$^{sis}$, a serine, and continues for 109 amino acids to a threonine residue at amino acid 175. The amino acid sequences preceding and following the B-chain homologous region of p28$^{sis}$ are not homologous to either the A- or B-chains of mature PDGF (Johnsson, ibid.) and represent portions of the B-chain precursor. In addition, PDGF and p28$^{sis}$ have been shown to be similar antigenically (Niman, ibid.; Robbins, ibid.). The v-sis gene product, p28$^{sis}$, a protein of approximately 226 amino acids, dimerizes and is proteolytically processed to a protein of approximately 20,000 Daltons (p20$^{sis}$) in SSV infected cells (Niman, ibid.; Robbins, ibid.). This 20,000 Dalton protein can be immunoprecipitated with antiserum against PDGF.

As noted above, previous attempts at expressing v-sis sequences in prokaryotes did not yield biologically active material. The v-sis gene product p28$^{sis}$, as well as PDGF itself, are secreted mammalian proteins. Within the present invention, it has been found that by utilizing the secretory pathway of eucaryotic cells to express the v-sis gene and B-chain derivatives of the v-sis gene, or other DNA constructions encoding PDGF analogs, biologically active material may be obtained. Expression and secretion of these gene products from a eucaryotic cell enable processing and assembly, which result in molecules with native and biologically active conformation.

The secretory pathways of eucaryotes are believed to be quite similar. In particular, mammalian cell and yeast cell secretory pathways are well characterized and are homologous. The presence of a secretory signal sequence on the expressed polypeptide is an important element in eucaryotes, due to its role in directing the primary translation product into the secretory pathway, thereby leading to proper processing and assembly. Provided that appropriate transcriptional promoter and secretory signal sequences are utilized, generally any eucaryote could express and secrete PDGF-analogs in a biologically active form.

An easily manipulable and well-characterized eucaryote is the yeast cell. For these reasons, yeast was chosen as a model example of an appropriate eucaryotic cell within the present invention. In accordance with the present invention, the yeast promoter is followed downstream by a DNA sequence which encodes a protein having substantially the same biological activity as PDGF. For example, DNA sequences encoding the 109 amino acids of the PDGF B-chain or the 104 amino acids of the A-chain were inserted into yeast extrachromosomal elements containing a yeast promoter capable of directing their expression. These extrachromosomal elements were transformed into yeast cells capable of expression and secretion of these biologically active PDGF analogs. In addition, variants and derivatives of the PDGF A- and B-chains, as well as combinations of the A- and B-chains, were also inserted into such a yeast extrachromosomal element.

DNA sequences which encode a protein having substantially the same structure and/or biological activity as PDGF include the v-sis gene or derivatives of the v-sis gene, or portions thereof, or the human cDNAs for the A-chain or the B-chain of PDGF or portions thereof. In addition, suitable DNA sequences include those which encode the A-chain or the B-chain of PDGF, such as genes which are constructed using synthetic oligonucleotides as well as those which encode variants and derivatives of the A-chain or the B-chain.

There are a variety of variants and derivatives which may be used within the present invention. For instance, amino acid substitutions may be made in either the A-chain or the B-chain which: (a) modify the three-dimensional structure of the particular chain without significantly effecting its biological activity; (b) modify the three-dimensional structure, resulting in an alteration of the biological activity; or (c) affect biological activity without significantly changing the three-dimensional structure. For example, amino acid number 98 in the B-chain may be changed from lysine to leucine, resulting in a monomersized molecule exhibiting biological activity. Alternatively, biologically active monomers may be obtained by changing cysteine residues involved in interchain disulfide bonds between the polypeptides of the dimer to an amino acid which will not form a disulfide bond. Molecules which are biologically active as monomers may permit greater therapeutic application. Monomer analogs can also be further manipulated without the requirement for the formation of a dimer to obtain biological activity. This will facilitate structural analysis, leading to the definition of an active receptor binding site, thereby allowing the design of additional therapeutic analogs.

Further, deletion of one or more amino acids can also result in a modification of the structure of the resultant molecule without significantly altering its biological activity. This can lead to the development of a smaller active molecule which would have broader therapeutic utility. For example, as described herein, one can remove amino terminal amino acids not required for biological activity. Similarly, carboxy terminal amino acids may be removed, while retaining biological activity.

In addition to performing amino acid substitutions or deletions, a variety of PDGF analogs which are hybrid molecules may be generated that exhibit biological activity. Given the high degree of amino acid sequence homology between the A- and B-chains, one skilled in the art can construct a variety of hybrid molecules between the A- and B-chains, or portions thereof, which may include polypeptides which are, in essence, mosaics of A- and B-chain sequences. By way of example, the hybrid molecule may contain an amino terminal A-chain sequence followed by B-chain sequence, or a B-chain sequence may be interposed between A-chain sequences at the amino and carboxyl termini. Such hybrids may further be useful in defining sequences which are critical for biological activity.

As a further alternative, the sequences of these hybrids may be modified, which results in molecules exhibiting biological activity. For example, one or more amino acid changes, such as a change at A-chain acid number 10 from a cysteine to a serine, results in a molecule retaining biological activity.

Further, combinations of the A- and B-chains or their derivatives may also be used within the present invention. The term "combinations," as used within the present invention, includes heterodimers composed of two different polypeptides; e.g., the A-chain and the B-chain. The constituent polypeptides of the heterodimer can be chosen from wild-type A-chain or B-chain or portions thereof, as well as variants or derivatives of the A-chain or B-chain. The DNA sequences to be utilized in the extrachromosomal element may be isolated, synthesized or constructed using standard recombinant DNA techniques.

The human PDGF B-chain cDNA may be isolated from a human cDNA library made from an appropriate source of messenger RNA by using the v-sis gene or a fragment thereof as a hybridization probe, or through use of oligonucleotide probes designed from the B-chain DNA sequence. A preferred source of mRNA is human umbilical vein endothelial cells. These cells can be cultured in vitro for short periods of time and are known to secrete PDGF into the culture medium (DiCorleto and Bowen-Pope, *PNAS* 80: 1919, 1983). The identity of this cDNA as that encoding PDGF may be verified by DNA sequencing.

Once an appropriate DNA sequence encoding a protein exhibiting PDGF-like biological activity is identified, the sequence is ligated to an appropriate promoter and secretory signal fragment. Promoters which may be utilized in yeast include the yeast alpha-factor (MFα1) promoter and the yeast triose phosphate isomerase (TPI) promoter. Promoters may also be obtained from other yeast genes, e.g., Alcohol Dehydrogenase 1 (ADH1), Alcohol Dehydrogenase 2 (ADH2). Appropriate promoters for other eucaryotic species may also be used and will be apparent to those skilled in the art. The constructions described herein were designed such that the PDGF-related gene products would be secreted from the yeast cell into the media. This was accomplished through use of the prepro secretory signal sequence of the yeast mating pheromone alpha-factor (Kurjan and Herskowitz, *Cell* 30: 933, 1982; Julius et al., *Cell* 36: 309, 1984; and Brake et al., *PNAS* 81: 4642, 1984), although other secretion signals may be used. To ensure the efficient transcription termination and polyadenylation of mRNA, a yeast terminator sequence, such as the triose phosphate isomerase terminator, was added. (Alber and Kawasaki, *J. Molec. Genet. Appl.* 1: 419, 1982.) Methods of ligation of DNA fragments have been amply described (Maniatis et al., *Molecular Cloning: A Laboratory Manual*, Cold Spring Harbor Laboratory 1982) and are well within the skill of those of ordinary skill in the art to perform. After preparation of the expression unit constructions, the constructs are inserted into an appropriate expression vector.

It is preferable to use an expression vector which is stably maintained within the host cell in order to produce more biological activity per culture. Suitable yeast expression vectors in this regard are the plasmids pCPOT and pMPOT2, which include the *Schizosaccharomyces pombe* gene encoding the glycolytic enzyme triose phosphate isomerase (POT1 gene). Inclusion of the POT1 gene ensures the stable maintenance of the plasmid in an appropriate host cell due to its ability to complement the corresponding gene deletion present within this host cell.

After preparation of the DNA construct incorporating the promoter, the alpha-factor secretory signal sequences, the appropriate DNA sequence encoding a molecule having PDGF-like biological activity, and the TPI terminator in an appropriate vector, the construct is transformed into the yeast host with a TPI deletion. Procedures for transforming yeast are well known in the literature.

The transformed yeast cells may be selected by growth on conventional complex medium containing glucose when the pCPOT or pMPOT2 vector is utilized. A conventional medium, such as YEPD (20 grams glucose, 20 grams Bacto-peptone, 10 grams yeast extract per liter), may be used. Once selected, transformants containing the appropriate expression constructions are grown to stationary phase on conventional complex media, the cells removed by centrifugation or filtration, and the medium concentrated. Noting that authentic human PDGF is a highly cationic and hydrophobic protein (Raines and Ross, ibid.; Antoniades, ibid.; Deuel et al., 1981, ibid.), it was expected that the yeast expressed, PDGF-related products would possess similar characteristics, allowing the use of ion exchange chromatography to be used in their purification.

Using a variety of assays, it can be demonstrated that spent media from yeast cultures expressing the pDGF analogs possess biological activities substantially identical to authentic human PDGF.

Expression of biologically active PDGF analogs in eucaryotic cells other than yeast cells can be achieved by a person skilled in the art through use of appropriate expression/regulatory signals. Transcriptional promoters capable of directing the expression of these sequences are chosen for their ability to give efficient and/or regulated expression in the particular eucaryotic cell type. Signal sequences capable of directing the gene product into the cell's secretory pathway are chosen for their function in the appropriate cell type. Other useful regulatory signals, such as transcription termination signals, polyadenylation signals and transcriptional enhancer sequences, are also chosen for their function in the appropriate cell type, the selection of which would be apparent to an individual skilled in the art.

The techniques of cell culture have advanced considerably in the last several years as have the number and varieties of mammalian cells which will grow in culture. Central to these advances is a better understanding of the nutritional requirements (i.e., hormones and growth factors) of cultured cells (Barnes and Sato, *Cell* 22: 649, 1980). The types of cells able to grow in culture can be crudely classified in two groups: normal and transformed. So-called "normal" cells are generally not immortal in culture, they do not form tumors when injected into animals, and they retain a normal diploid karyotype. Normal cells may also retain much of their differentiated character in culture. Within the category of normal cells are those which will only grow for a limited number of generations in culture, termed "cell strains" or "primary cultures." Some normal cell lines, while not meeting all the criteria of transformation, may grow indefinitely in culture. Transformed cells are immortalized for growth in culture, typically have lost their differentiated phenotype, and have acquired karyotypic aberrations. They may also be independent of anchorage for growth and induce tumors when injected into the appropriate host animal. Cells in any of these categories which grow in vitro and possess PDGF receptors will be responsive to the PDGF analogs of this invention.

To summarize the examples which follow, EXAMPLE I demonstrates the construction of a v-sis subclone of pSSV-11 in the E. coli replicating plasmid pUC13, subsequently designated pVSIS/Pst. EXAMPLE II demonstrates the construction of the plasmid pVS$\alpha$, which includes the ligation of v-sis to the MF$\alpha$1 promoter and secretory signal sequence. EXAMPLE III demonstrates the oligonucleotide-directed deletion mutagenesis of the first 195 base pairs of the v-sis gene using a technique which employs single stranded bacteriophage M13 in order to eliminate the first sixty-six amino acids of the v-sis gene product, $p28^{sis}$, which are not homologous to the B-chain of PDGF. A resulting phage with the correct deletion was designated mllvs2$\alpha$. EXAMPLE IV demonstrates the construction of the expression vector pVSBm. EXAMPLE V demonstrates the transformation of yeast host cells. EXAMPLE VI demonstrates the construction of pSB1. EXAMPLE VII demonstrates the construction of variants and derivatives of the B-chain. EXAMPLE VIII demonstrates the construction of variants and derivatives of the A-chain. EXAMPLE IX demonstrates the construction of yeast expression vectors for A- and B-chain variants and derivatives. EXAMPLE X demonstrates a method for producing an A-B heterodimer in yeast. EXAMPLE XI demonstrates the concentration of the spent yeast growth media from transformed cultures and subsequent analysis for PDGF-like material. Clear evidence is presented that these yeast media containing the PDGF analogs described herein possess substantially the same biological activity as authentic human PDGF.

The following examples are offered by way of illustration, and not by way of limitation.

EXAMPLE I

Subcloning of v-sis from pSSV-11

The SSV retroviral genome was cloned from SSV-11 nonproductively infected normal rat kidney (NRK) cells which had SSV integrated into their genome (Devare et al.,1982, ibid.). The SSV DNA was isolated as a 5.8 kilobase (kb) Eco RI fragment and subsequently inserted into the plasmid pBR322, resulting in the clone pSSV-11. This clone was obtained from S. Aaronson (National Institutes of Health, Bethesda, Md.).

FIG. 1A is a schematic restriction map of the 5.8 kilobase proviral genome of SSV. Only the restriction sites relevant to the present invention are indicated. The open box designates the $p28^{sis}$ coding portion of the v-sis gene.

FIG. 1B depicts the nucleotide sequence of the v-sis gene and some flanking SSV sequences. The v-sis gene is inserted 19 nucleotides 3′ of the putative ATG initiation codon of the envelope (env) gene of SSV (Devare et al., 1982, ibid.). It is believed that transcription and translation of v-sis sequences are directed by SSV sequences resulting in an env-sis fusion protein. The nucleotide sequence shown in FIG. 1B is corrected from that published by Devare et al. in 1982 (ibid.). The corrections include those made by Devare et al. in 1983 (ibid.) and by the inventors herein. The original numbering scheme of Devare et al. (1982, ibd.) is retained here for ease of reference. The numbers assigned to the restriction sites in FIG. 1A are from FIG. 1B.

A subclone of pSSV-11 (FIG. 2) containing a portion of the v-sis gene was constructed in the *E. coli* replicating plasmid pUC13 (Vieira and Messing, *Gene,* 19: 259, 1982; and Messing, *Meth. in Enzymology* 101: 20, 1983). Five micrograms (ug) of pSSV-11 was digested with the restriction endonuclease Pst I and the 1.2 kb fragment containing sequences numbered 454–1679 (FIG. 1) was purified by agarose gel electrophoresis (0.9%) and extracted from the gel with cetyltrimethylammonium bromide (CTAB) plus butanol (Langridge et al., ibid.). Two ug of pUC13 was also digested with Pst I, phenol/chloroform ($CHCl_3$) extracted and ethanol (EtOH) precipitated. Forty ng of the 1.2 kb vssis fragment and 50 ng of Pst I cut pUC13 were ligated overnight at room temperature with 40 units (u) of $T_4$ DNA ligase. The ligation mixture was used to transform *E. coli* K-12 strain JM83 (Messing, Recombinant DNA Technical Bulletin, NIH Publication No. 79-009, 2, No. 2, 43–48, 1979) in the presence of 5-bromo,4-chloro, 3-indolyl-$\beta$-D-galactoside (X-gal) and isopropyl $\beta$-D-thiogalactoside (IPTG). Plasmid DNA prepared from ampicillin-resistant white colonies was digested with Pst I to verify the presence of the insert and the resulting plasmid was designated pVSIS/Pst.

EXAMPLE II

Construction of the Plasmid pVS$\alpha$

A. Preparation of v-sis for Fusion to MF$\alpha$1.

Six hundred ug of plasmid pSSV-11 (FIG. 2) was digested with restriction endonucleases Bam HI and Pvu II in 200 microliters (ul) of 50 mM NaCl, 10 mM $MgCl_2$, 10 mM Tris pH 7.5 (medium salt buffer), and 100 ug/ml bovine serum albumin (BSA), overnight at 37° C. The digestion products were electrophoresed through a 1.1% agarose gel and the 1100 base pair (bp) Bam HI—Pvu II fragment (FIG. 2) cut out, extracted and EtOH precipitated. The DNA pellet was dissolved in 75 ul Hph I buffer to which was added 20 ul of 1 mg/ml BSA and 5 ul Hph I. After overnight digestion at 37° C., the mixture was electrophoresed through a 1.25% agarose gel and the 396 bp Hph I—Pvu II fragment isolated from the gel and EtOH precipitated. The DNA pellet was dissolved in 30 ul of Klenow buffer (6 mM Tris pH 7.5, 6 mM $MgCl_2$, 60 mM NaCl) and the 3′ overhanging nucleotide at the Hph I cleavage site removed by treatment with 5 u of Klenow polymerase for 5 minutes at 37° C. One ul of a mixture containing all four deoxyribonucleotides each at 1 mM was added and the reaction mixture incubated an additional 10 minutes. After phenol/$CHCl_3$/ether ($Et_2O$) extraction and EtOH precipitation, the DNA pellet was dissolved in 30 ul of medium salt buffer and digested with 5 u of Bgl II for three hours at 37° C. The DNA was electrophoresed through a 1.25% agarose gel and the 269 bp Hph I—Bgl II fragment extracted and EtOH precipitated. The Hph I cleavage terminus of this Klenow blunted fragment begins with the tri-nucleotide sequence

5′ATG . . . (FIG. 2)
3′TAC . . .

B. MF$\alpha$1 Promoter and Secretory Leader Fragment.

Plasmid p192 (FIG. 3) comprises a portion of the gene for the yeast mating pheromone $\alpha$-factor (MF$\alpha$1 gene) cloned in the bacterial plasmid pUC13 (Vieira and Messing, ibid.; and Messing, *Meth. in Enzymology* 101: 20, 1983). Cloning of the MF$\alpha$1 gene from a genomic library has been described by Kurjan and Herskowitz (ibid.). The gene was isolated in this laboratory in a similar manner, using as starting material a yeast genomic library of partial Sau 3A fragments cloned into the Bam HI site of Yep13 (Nasmyth and Tatchell, *Cell* 19: 753, 1980). From this library, a plasmid was isolated which expressed $\alpha$-factor in a diploid strain of yeast homozygous for the mat$\alpha$ 2–34 mutation (Manney et al.,

Figure 3:
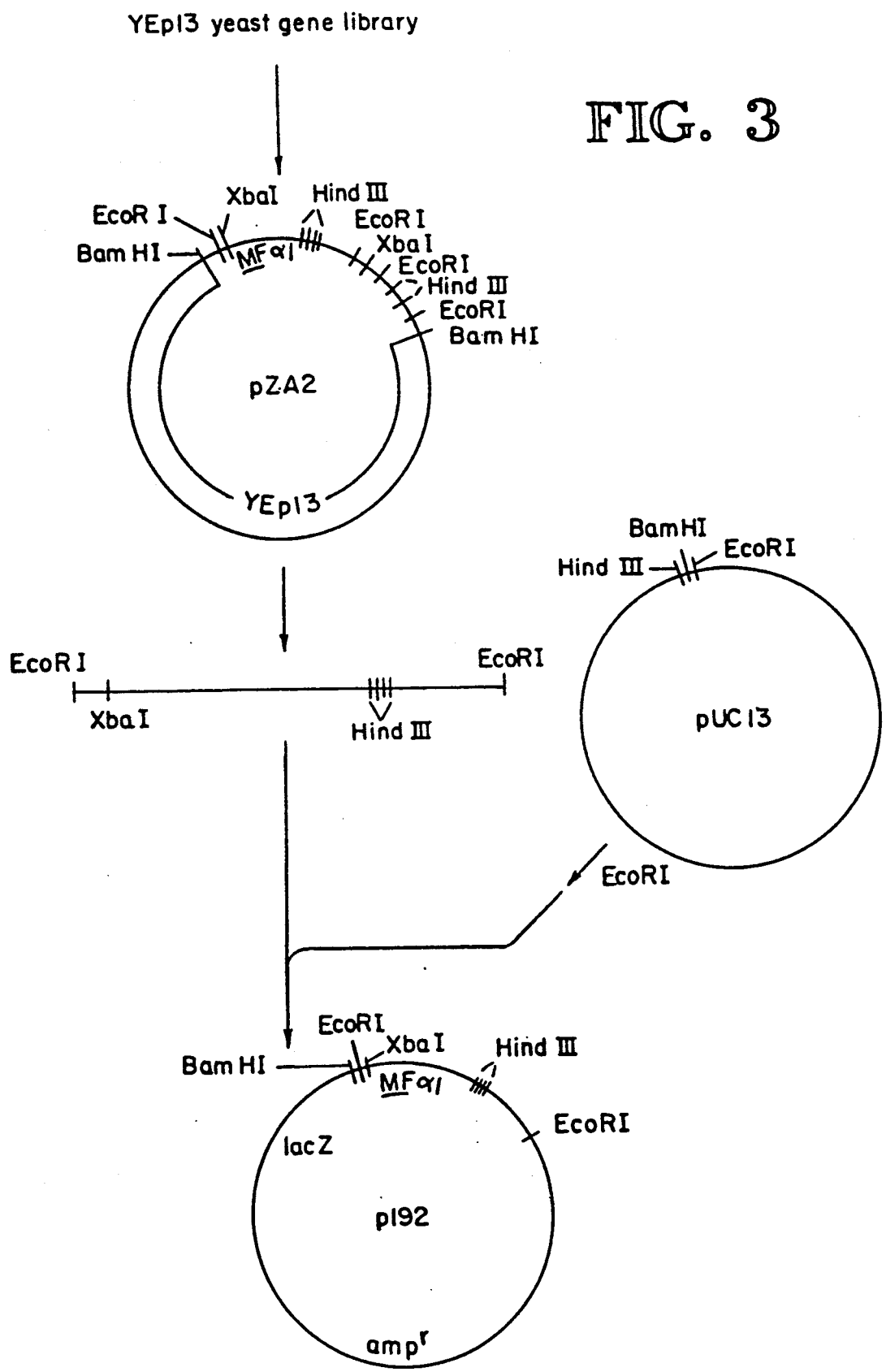
FIG. 3 illustrates the construction of plasmid p192.

*J. Cell Biol* 96: 1592, 1983). The clone contained an insert overlapping with the MFα1 gene characterized by Kurjan and Herskowitz (ibid). This plasmid, known as pZA2 (FIG. 3), was cut with Eco RI and the 1700 bp fragment comprising the MFα1 gene was purified. This fragment was then subcloned into the Eco RI site of pUC13 to produce the plasmid p192.

Fifteen ug of plasmid p192 was digested in 30 ul of medium salt buffer with 20 units of Hind III overnight at 37° C. The reaction mixture was diluted to 60 ul with Klenow buffer and the four deoxyribonucleotides added to a final concentration of 50 uM each. Ten units of Klenow polymerase were added to the ice-cold mixture and incubation allowed to proceed 12 minutes at 15° C. Following phenol/CHCl$_3$/Et$_2$O extraction, the aqueous phase was concentrated by lyophilization to a volume of 10 ul and digested with 20 units of Eco RI for 70 minutes at 37° C. The products were electrophoresed through a 0.9% agarose gel and the 1.2 kb Eco RI—Hind III (blunted) MFα1 fragment extracted and EtOH precipitated. This DNA fragment contains the transcriptional promoter and secretory signal sequences of MFα1.

C. Preparation of v-sis 3' Sequences and Cloning Vector pUC12; Fragment Ligation.

Twenty ug of plasmid pVSIS/Pst was digested with Bgl II and Xba I in 40 ul of medium salt buffer. Subsequent electrophoresis through 1% agarose, extraction of the DNA and EtOH precipitation provided the purified v-sis 756 bp Bgl II—Xba I fragment (FIG. 2). *E. coli* replicating plasmid pUC12 (5 ug) was digested with Eco RI and Xba I and gel-purified as above (FIG. 2).

Referring to FIG. 2, equimolar amounts of the four DNA fragments described above, adjusted to 10 ng of the 296 bp Hph I—Bgl II v-sis fragment, were mixed in 15 ul of ligase buffer (6 mM Tris pH 7.6, 6.6 mM MgCl$_2$, 0.4 mM ATP, 2 mM spermidine, 20 mM DTT, and 100 ug/ml BSA) and ligated with 40 units of T$_4$ DNA ligase overnight at 14° C. The reaction mixture was brought to room temperature, an additional 150 units of T$_4$ ligase added, and incubated 10 more hours. Seven ul of the ligation mix was used to transform *E. coli* K-12 RR1 (ATCC #31343; Bolivar, E. et al., *Gene* 2: 95, 1977), and ampicillin-resistant transformants selected. Plasmid DNA was prepared from twelve such bacterial colonies and digested with Xba I. Two clones gave a 2.2 kb band predicted by the proper fragment alignment (FIG. 2). Further analysis of these by Bgl II—Xba I restriction mapping gave expected bands of approximately 1.5 kb from the MFα1/v-sis fusion and 760 bp for the Bgl II—Xba I v-sis fragment. DNA sequence analysis verified the desired nucleotide sequence at the MFα1/v-sis junction. The resultant plasmid was designated pVSα.

EXAMPLE III

Construction of mllVS2α

Homology between the v-sis protein p28$^{sis}$ and PDGF begins at amino acid 67 of p28$^{sis}$, a serine residue corresponding to the NH$_2$ terminal residue of the PDGF B-chain (Johnsson, ibid.)

Proteolytic processing of the MFα1 primary translation product occurs at the Lys-Arg cleavage signal 85 amino acids from the initiator methionine (Kurjan and Herskowitz, ibid.). A v-sis derivative was constructed in which the first 66 codons of p28$^{sis}$ were removed such that serine residue 67 of v-sis immediately follows the MF 1 Lys-Arg processing signal.

Figure 4:
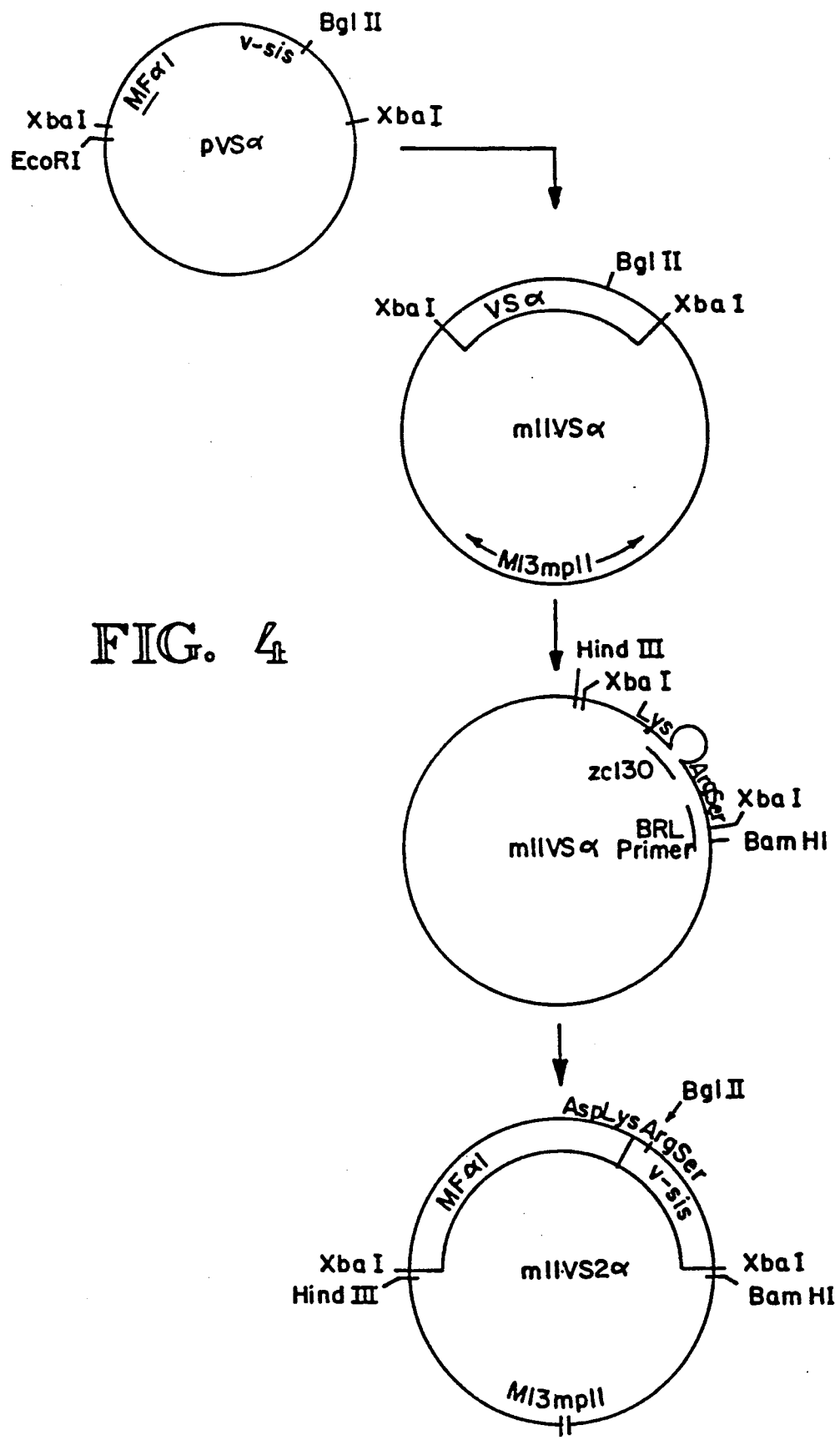
FIG. 4 illustrates the oligonucleotide-directed deletion mutagenesis of the amino terminal 66 v-sis codons.

Referring to FIG. 4, approximately 40 ng of the gel purified 2.2 kb Xba I fragment of pVS was ligated with 120 ng of Xba I digested, alkaline phosphatase-treated M13mpll DNA (Messing, *Meth. in Enzymology*, ibid.). The ligation mixture was used to transform *E. coli* K-12 strain JM101 (ATCC 33876) in the presence of X-gal and IPTG. Isolated white plaques were picked and used to infect 3 ml cultures of log phase growth JM101 cells. Replicative Form (RF) DNA was prepared and clones identified which carried the insert fragment in the same orientation as the positive (+) strand form of the single-stranded mature phage. Single-stranded phage DNA was prepared from one such clone and designated mllVSα.

To precisely remove codons 1-66 of v-sis, oligonucleotide-directed mutagenesis was performed essentially according to the two-primer method of Zoller et al. (*Manual for Advanced Techniques in Molecular Cloning Course*, Cold Spring Harbor Laboratory, 1983). Oligonucleotide ZC 130 3' AGAAACC-TATTTTCCTCGGACCCA 5' was synthesized on an Applied Biosystems 380-A DNA synthesizer. Fifty pmoles of ZC 130 was kinased in 10 ul of kinase buffer (BRL) with 4 units of T$_4$ polynucleotide kinase for 45 minutes at 37° C. The enzyme was inactivated by heating at 65° C. for 10 minutes.

One-half pmole of mllVSa was annealed with 1 pmole of kinased ZC 130 and 1.5 pmoles of universal sequencing primer (BRL) using conditions described (Zoller et al., ibid.), except that the annealing mixture was first heated to 65° C. for 10 minutes, shifted to 37° C. for 10 minutes, and then quickly chilled on ice. The annealed mixture was then treated with Klenow polymerase as described by Zoller et al. (ibid.) to create circular duplex DNA. Portions of the elongation mixture were used to transform *E. coli* K12 JM101 cells. The resulting phage plaques were screened for the proper deletion by transfer onto nitrocellulose filters and subsequent hybridization with $^{32}$P phosphorylated ZC 130 at 65° C. Correctly juxtaposed sequences formed stable duplexes with the radioactive probe at the stringent hybridization temperature employed. Approximately 1% of the transformants screened gave positive signals by autoradiography. Ten clones were plaque-purified and RF DNA was prepared for restriction enzyme analysis. Five isolates showed the expected decrease in size of 195 bp to the 1450 bp Hind III—Bgl II fragment (FIG. 4). DNA sequence analysis of two isolates confirmed the correct fusion junction had been made, thus maintaining the proper translational reading frame. One of these phage was designated mllVS2α.

EXAMPLE IV

Construction of pVSBm

A. Construction of Plasmids YEpVSα and YEpVS2α.

Yeast Replicating Vector YEp13 (Broach et al., *Gene* 8: 121, 1979) was used as an expression vehicle for v-sis-derived constructions described in Examples II and III. YEp13 is a multicopy extrachromosomal plasmid containing a 2 micron replication origin and the yeast LEU2 gene. This allows for selection of the plasmid in yeast strains possessing a defective chromosomal LEU2 gene when grown on synthetic medium lacking leucine. Addition of yeast terminator sequences to foreign genes expressed in yeast ensures efficient transcription termination and polyadenylation of mRNA. The v-sis expression units VSα and VS2α were placed adjacent to the TPI terminator fragment which was previously cloned into YEp13 (below).

Figure 5:
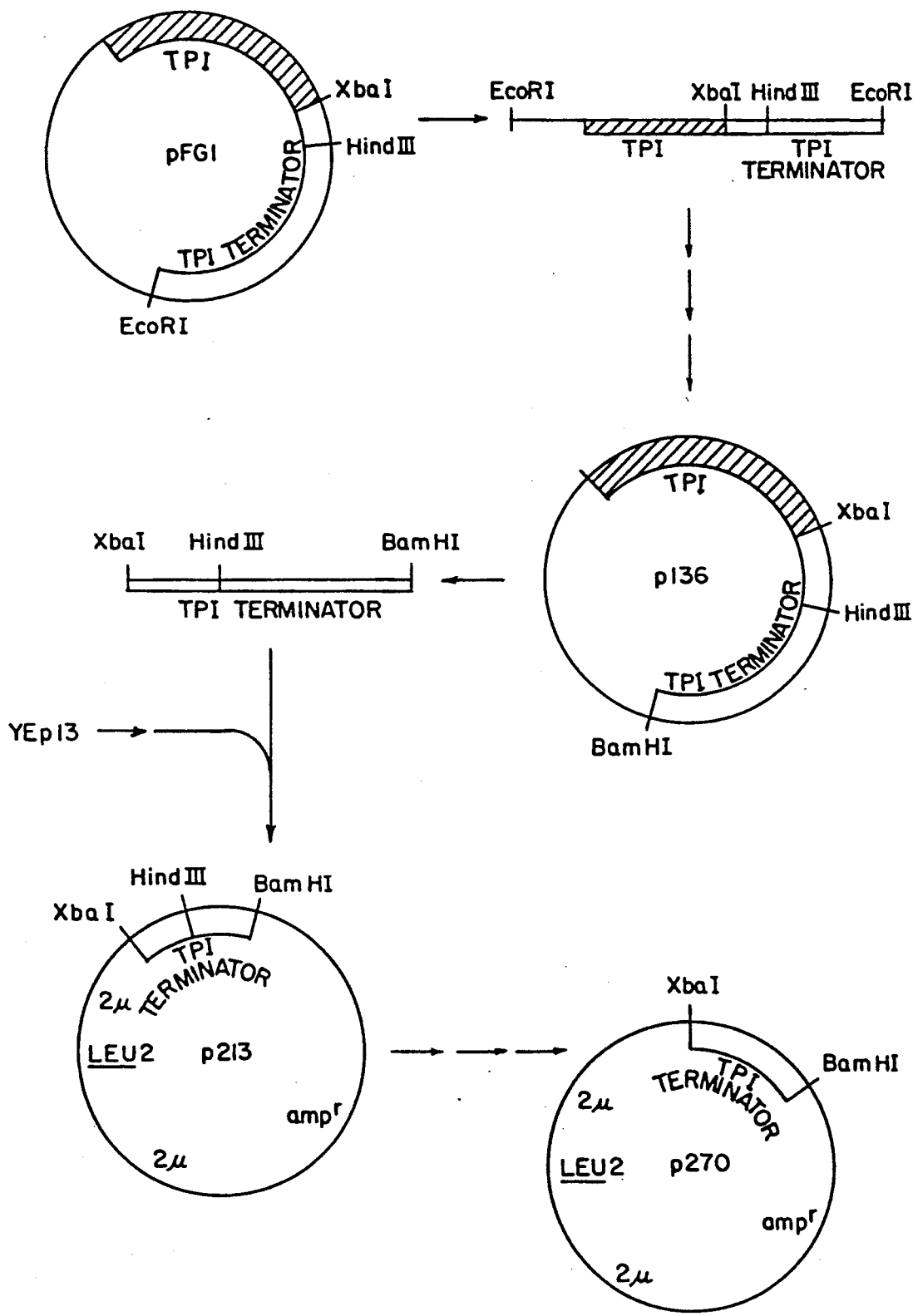
FIG. 5 illustrates the construction of plasmid p270.

Plasmid p270 (see FIG. 5) contains the transcription terminator region of the yeast triose phosphate isomerase (TPI) gene. It was constructed in the following manner. The yeast TPI terminator fragment was obtained from plasmid pFG1 (Albert and Kawasaki, ibid.). It encompasses the region from the penultimate amino acid codon of the TpI gene to the Eco RI site approximately 700 base pairs downstream. A Bam HI site was substituted for this unique Eco RI site of pFG1 by first cutting the plasmid with Eco RI, then blunting the ends with DNA polymerase I (Klenow fragment), adding synthetic Bam HI linkers (CGGATCCA), and re-ligating to produce plasmid p136. The TPI terminator was then excised from p136 as a Xba I—Bam HI fragment. This fragment was ligated into YEp13 (Broach et al., ibid.), which had been linearized with Xba I and Bam HI. The resulting plasmid is known as p213. The Hind III site was then removed from the TPI terminator region of p213 by digesting the plasmid with Hind III, blunting the resultant termini with DNA polymerase I (Klenow fragment), and recircularizing the linear molecule using T$_4$ DNA ligase. The resulting plasmid is p270.

Alternatively, p270 may be constructed by digesting plasmid pM220 (see below) with Xba I and Bam HI, purifying the TPI terminator fragment (~700 bp) and inserting this fragment into Xba I and Bam HI digested YEp13.

Figure 6:
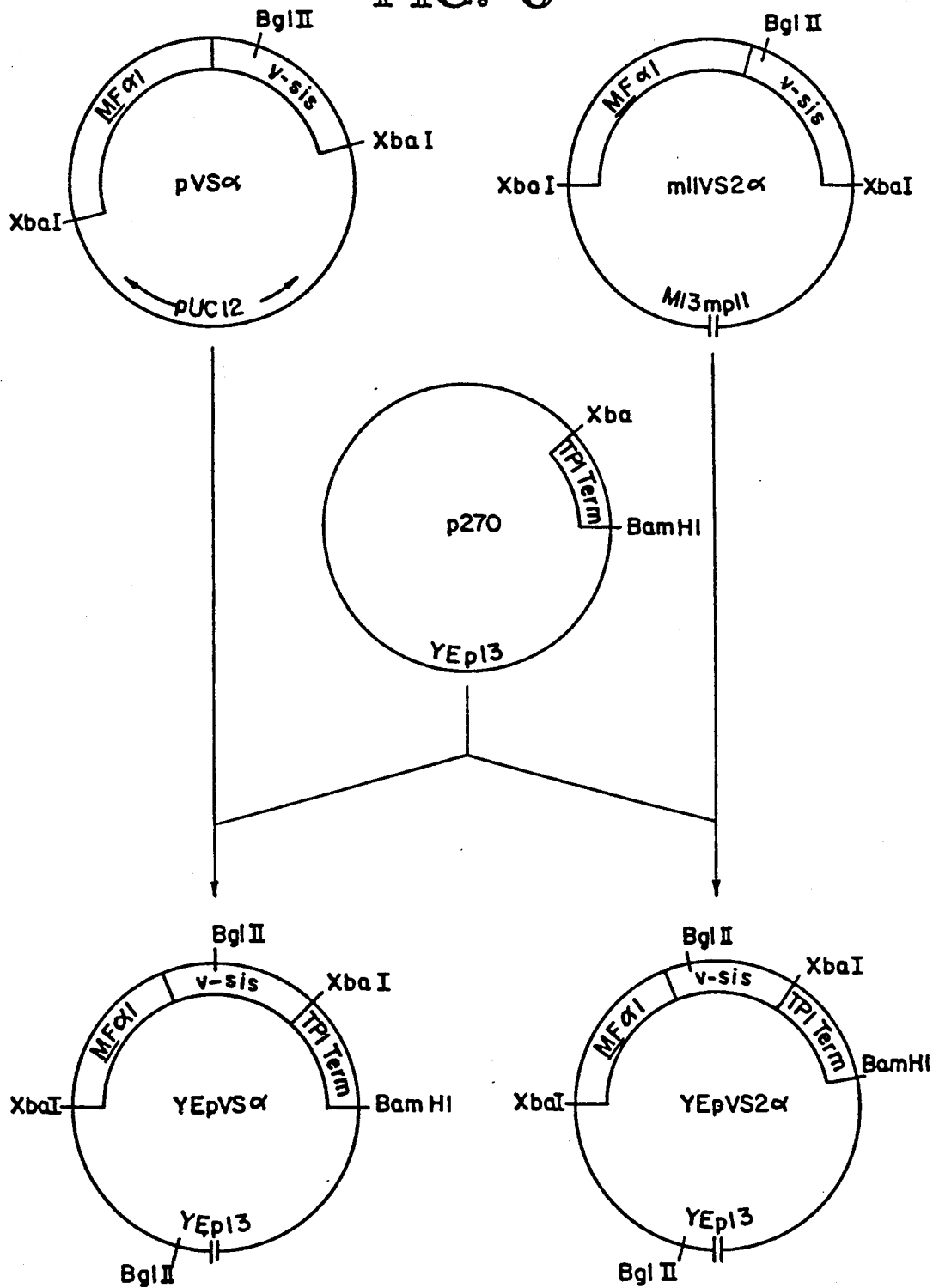
FIG. 6 illustrates the insertion of v-sis expression units upstream of the TPI terminator.

Referring to FIG. 6, plasmid p270 DNA was digested with Xba I and treated with calf alkaline phosphatase to prevent religation of the cohesive vector ends. V-sis expression units VSα and VS2αwere prepared by XbaI digestion and agarose gel purification of pVSα and mllvs2α, respectively. Each of the isolated fragments was ligated with an approximately equimolar amount of phosphatased p270 vector in the presence of 40 units of T$_4$ DNA ligase and the ligation mixtures transformed into E. coli K-12 RR1. Plasmid DNA was prepared from ampicillin-resistant colonies and restriction enzyme analysis performed in order to identify clones which possessed the TPI terminator adjacent to 3' v-sis sequences. Presence of 3.3 kb or 3.1 kb Bgl II fragments after gel electrophoresis indicated the correct orientation of YEpVSα and YEpVS2α, respectively.

B. Construction of the Plasmid pVSB.

Because the product encoded by pVS2α is larger than authentic human PDGF B-chain and because a smaller product might result in higher expression levels in a transformed yeast host cell, a vector was constructed comprising the v-sis sequence of pVS2 ' truncated at the 3' end. The polypeptide encoded by this sequence comprises amino acids 67 to 175 of p28$^{sis}$ and is homologous to the B-chain of PDGF.

Figure 7:
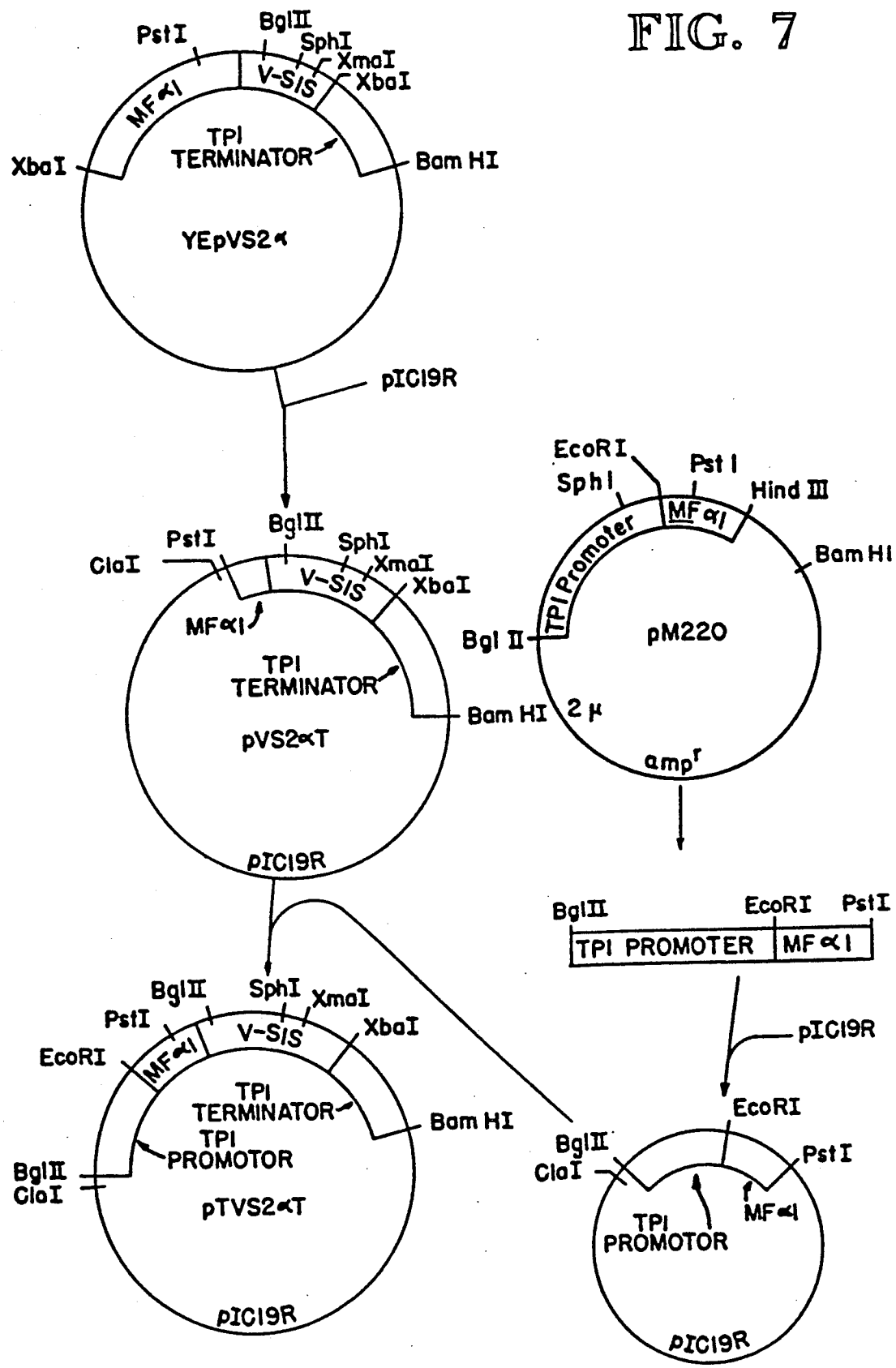
FIG. 7 illustrates the construction of plasmid pTVS2αT.
Figure 8:
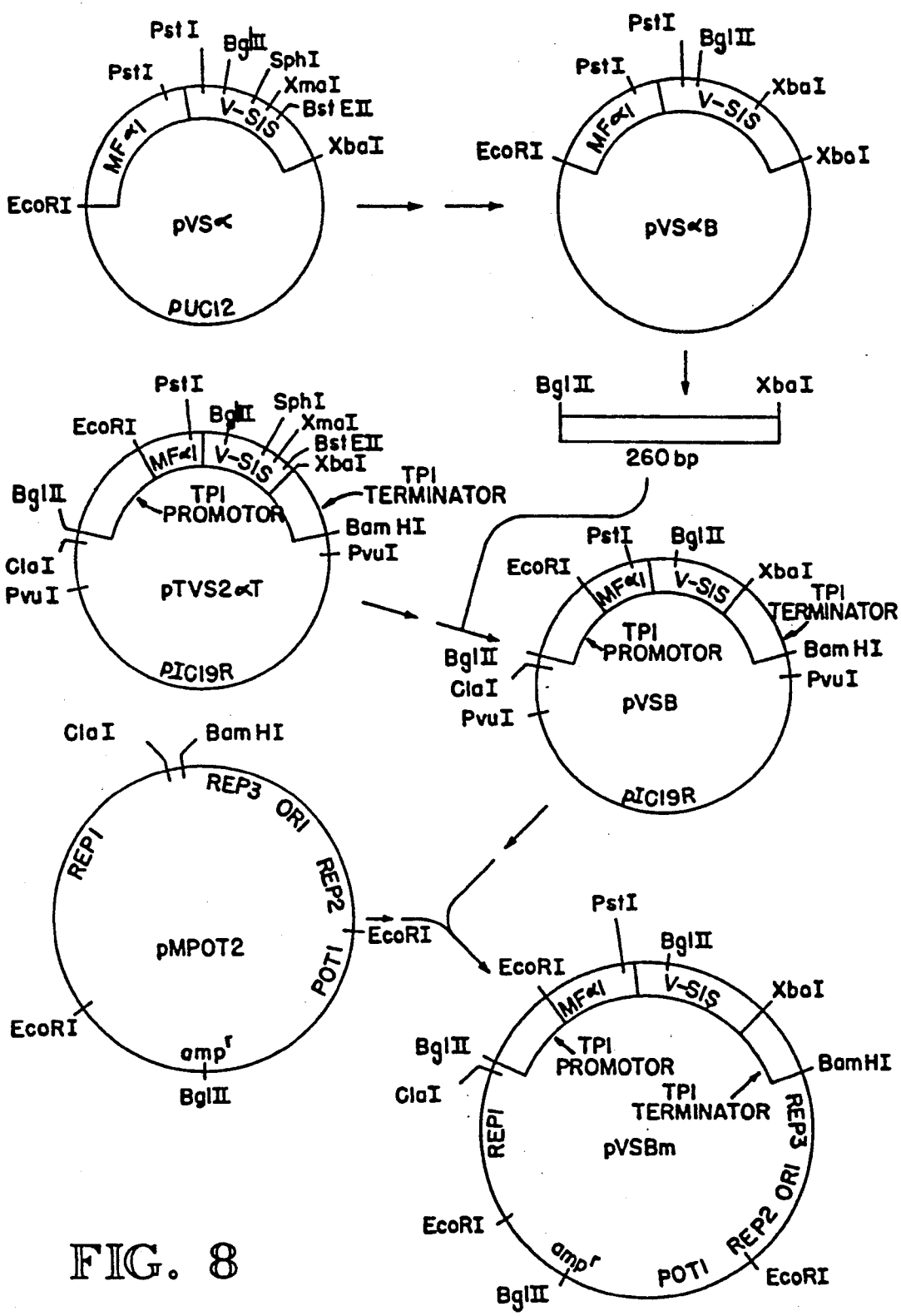
FIG. 8 illustrates the construction of a B-chain expression unit VSB and its introduction into the pMPOT2 vector.

An expression vector containing this "B-chain" sequence was constructed by combining elements of the pVS2α expression unit with a partial v-sis gene and a synthetic double-stranded DNA fragment encoding amino acids 158 to 175 of p28$^{sis}$. This synthetic fragment was designed to substitute preferred yeast codons for many of the 13 v-sis codons it replaces, and to supply a stop codon at the end of the coding sequence. The construction of this vector is illustrated in FIGS. 7 and 8.

Plasmid YEpVS2α was digested with Pst I and Bam HI; and the 1.8 kb fragment, comprising the partial MFα1, v-sis, and TPI terminator sequences, was purified by agarose gel electrophoresis. Plasmid pICl9R (Marsh et al., Gene 32: 481–486, 1984), comprising the polylinker shown in Chart 1 inserted into the Hind III site of pUC19 (Norrander et al., Gene 26: 101–106, 1983), was digested with Pst I and Bam HI, and the vector fragment was gel-purified and joined to the 1.8 kb fragment from pVS2α to produce plasmid pVS2αT.

CHART 1

GAATTCATCGATATCTAGATCTCGAGCTCGCGAAAGCTT

| Eco RI | Eco RV | Bgl II | Sac I | Hind III |
|--------|--------|--------|-------|----------|
| Cla I  | Xba I  | Xho I  | Nru I |          |

The S. cerevisiae TPI promoter was used to control expression of VS2α sequences in a yeast expression vector. Plasmid pM220 contains the TPI promoter fused to the MFα1 signal sequence. E. coli RRI transformed with pM220 has been deposited with American Type Culture Collection under accession number 39853.

Plasmid pM220 was digested with Bgl II and Pst I (FIG. 7), and the ca. 1 kb fragment comprising the TPI promoter and the 5' portion of the MFα 1 sequence was isolated and cloned in Bgl II+Pst I digested pICl9R. The resultant plasmid was digested with Cla I and Pst I, and the TPI promoter—MFα1 fragment was gel-purified. Plasmid pVS2αT was then cut with Cla I and Pst I and joined to the TPI promoter—MFα1 fragment. The correct construct was identified by the presence of a 2.6 kb Cla I—Bam HI fragment and was designated pTVS2αT.

Ten ug of plasmid pVSα was digested with Xma I and Sph I (FIG. 8) to completion. The resulting ca. 4.9 kb vector fragment, which also comprises most of the v-sis sequence, was purified by agarose gel electrophoresis, extraction of the DNA and EtOH precipitation.

In order to supply a new 3' terminus for the v-sis sequence, a double-stranded DNA fragment was constructed from oligonucleotides synthesized on an Applied Biosystems Model 380-A DNA synthesizer. 0.7 pmole of oligonucleotide ZC299 (Table 1) was heated with an equimolar amount of oligonucleotide ZC300 in a volume of 10 ul containing 40 mM NaCl for 5 minutes at 65° C.

TABLE 1

ZC299: 5'TAAG TGT GAA ATC GTT GCC GCG GCT AGA GCT GTT ACC TAA TCT AGA3'
ZC300: 3'GTACA TTC ACA CTT TAG CAA CGG CGC CGA TCT CGA CAA TGG ATT AGA TCT GGCC5'

The mixture was then incubated at 37° C. for 5 minutes and allowed to cool to room temperature. 0.2 pmole of the purified 4.9 kb vector fragment was added, the mixture ligated for 18 hours at 12° C. and used to transform E. coli HB101 (ATCC 33694) to ampicillin resistance. DNA was prepared from ampicillin-resistant colonies and digested with Bgl II and Xba I. After electrophoresis through agarose, the desired clone (known as pVSaB) was identified by loss of a ca. 750 bp Bgl II—Xba I fragment and appearance of two smaller fragments of approximately 500 and 260 bp.

Approximately 8 ug of plasmid pTVS2αT (FIG. 8) were digested to completion with Xba I in a volume of 10 ul. The volume was increased to 40 ul with Bg II buffer, and 6 units of Bgl II were added and the mixture was incubated at 37° C. Ten ul aliquots were removed to a stop buffer containing 50 mM EDTA at 15 and 30 minutes, and the remaining 20 ul stopped at 45 minutes. The resulting mixtures were separated by electrophoresis through 0.7% agarose. The ca. 4.6 kb Bgl II—Xba I vector fragment was cut out, extracted from the gel, and EtOH precipitated. Plasmid pVSαB was digested with Bgl II and Xba I, and the ca. 260 bp fragment containing the synthetic 3' terminus and stop codon was isolated by electrophoresis through agarose, subsequent extraction from the gel, and EtOH precipitation.

The 4.6 kb Bgl II—Xba I vector fragment from pTVS2αT and the 260 bp Bgl II—Xba I fragment from pVSαB were ligated in the presence of T$_4$ DNA ligase for 7 hours at room temperature. The reaction mixture was used to transform E. coli HB101 to ampicillin resistance. DNA was prepared from transformants and the presence of the desired insert was confirmed by screening for a 550 bp Pst I—Xba I band on an agarose gel. A plasmid having the correct configuration was designated pVSB.

There are several alternative approaches which can be used to construct plasmid pVSB. The essential elements of pVSB include: the TPI promoter/alpha-factor fusion, which can be obtained from plasmid pM220, the B-chain coding sequence (base 551 through 877 of FIG. 1B) of the v-sis gene, which is widely available, and the TPI terminator, which can be obtained from plasmid p270. Someone skilled in the art could develop several strategies to arrive at pVSB using these elements.

C. Construction of pMPOT2.

In order to achieve maximal protein production from a yeast culture, it is desirable to use expression vehicles which are very stably maintained in the host cell. Plasmid pCPOT is such a preferred expression vehicle.

E. coli HB101 transformed with pCPOT has been deposited with American Type Culture Collection under accession number 39685. Plasmid pCPOT comprises the 2 micron circle genome (Hartley and Donelson, Nature 286: 860, 1980), E. coli plasmid pBR322 replication and selection sequences, and the Schizosaccharomyces pombe DNA sequences encoding the glycolytic enzyme triose phosphate isomerase (POT1). Presence of the POT1 gene in pCPOT ensures stable maintenance of the plasmid in the appropriate host background during growth on nonselective medium utilizing glucose as a carbon source.

For expression of the v-sis derivatives in yeast, a stable expression vector comprising the REP1, REP2, REP3 and ori sequences from yeast 2 micron DNA and the Schizosaccharomyces pombe triose phosphate isomerase (POT1) gene was constructed. The POT1 gene provides for plasmid maintenance in a transformed yeast host grown in complex media if such host is defective for triose phosphate isomerase.

The POT1 gene was obtained from the plasmid pFATPOT. S. cerevisiae strain E18 transformed with pFATPOT has been deposited with ATCC under accession number 20699. The plasmid may be purified from the host cells by conventional techniques. The POT1 sequence was removed from pFATPOT by digestion of the plasmid with Sal I and Bam HI. This ~1600 bp fragment was then ligated to pIC19R, which had first been linearized by digestion with Sal I and Bam HI. The Bam HI, Pst I and Sal I sites in the resultant plasmid were destroyed in two steps to produce plasmid pICPOT*. The Pst I and Sal I sites were removed by cutting with Pst I and Sal I; the ends were blunted by digesting the Pst I 3' overhang with DNA polymerase I (Klenow fragment) and filling in the Sal I 5' overhang with Klenow fragment. The blunt ends were then ligated. The Bam HI site was then removed by cutting the plasmid with Bam HI, filling in the ends with DNA polymerase I (Klenow fragment) and religating the blunt ends.

The 2u sequences were obtained from the plasmids YEp13 (Broach et al., Gene 8: 121–133, 1979) and Cl/1. Cl/1 was constructed from pJDB248 (Beggs, Nature 275: 104–109, 1978) by removal of the pMB9 sequences by partial digestion with Eco RI and replacement by Eco RI-cut pBR322. The REP3 and ori sequences were removed from YEp13 by digestion with Pst I and Xba I and gel purification. REP2 was obtained from Cl/1 by digestion with Xba I and Sph I and gel purification. The two fragments were then joined to pUC18 (Norrander et al., Gene 26: 101–106, 1983) which had been linearized with Pst I and Sph I to produce plasmid pUCREP2,3. REP1was obtained from Cl/1 by digestion with Eco RI and Xba I and gel purification of the 1704 bp fragment. The Eco RI—Xba I fragment was cloned into pUC13 which had been linearized with Eco RI and Xba I. The resultant plasmid was designated pUC13-+REP1. The pUC13+REP1 plasmid was cut with Hind II and ligated in the presence of Eco RI linkers (obtained from Bethesda Research Laboratories). The REP1 gene was then removed as an Eco RI fragment of approximately 1720 bp. This Eco RI fragment was cloned into pIC7 (Marsh et al., ibid.), which had been linearized with Eco RI and Xba I. The resultant plasmid was designated pICREP1#9.

To construct the final expression vector pMPOT$_2$ (FIG. 8), pICPOT* was linearized by a partial Hind III digestion and complete Sst I digestion. Plasmid pUCREP2,3 was cut with Hind III and Sst I, and the fragment comprising REP2, REP3 and ori sequences was gel-purified and joined to the linearized pICPOT*. The resultant plasmid, comprising REP2, REP3, ori, POT1 and amp$^r$ sequences, was designated pMPOT1. REP1 was then removed from pICREP1 as a Bgl II—Nar I fragment and was ligated to pMPOT1, which had been cleaved with Bgl II and Nar I. The product of this ligation was designated pMPOT$_2$ (deposited with ATCC, accession number 20744). Plasmid pMPOT$_2$ was digested with Cla I and Bam HI, and the vector fragment was purified as above.

D. Insertion of VSB expression unit into pMPOT$_2$.

Plasmid pVSB was digested with Cla I and Bam HI, and the 2.2 kb fragment containing the "B-chain" expression unit purified by agarose gel electrophoresis and EtOH precipitation. Plasmid pMPOT2 was also digested with Cla I and Bam HI. The fragments were ligated overnight at room temperature in the presence of T$_4$ DNA ligase and the reaction mixture used to transform E. coli HB101 to ampicillin resistance. DNA was prepared from transformants and the presence of the insert verified by digestion with Cla I and Bam HI and agarose gel electrophoresis. The resulting expression vector was designated pVSBm (FIG. 8).

EXAMPLE V

Yeast Transformation

Plasmids pVSBm and pMPOT2 were used to transform *S. cerevisiae* n E18 #9 by conventional methods. Strain E18 #9 is a diploid produced by crossing strains E11-3c (ATCC No. 20727) (Δtpi::LEU2 pep4 leu2 MATα) and Δtpi29 (Δtpi::LEU2 pep4 leu2 his MATa.). Δtp29 is produced by disrupting the triose phosphate isomerase gene of strain E2-7b (ATCC No. 20689), essentially as described by Rothstein (*Meth. in Enzymology* 101: 202–210, 1983).

EXAMPLE VI

Construction of pSB1

In order to begin replacing B-chain coding sequence with A-chain sequence in the pVSB vector, a convenient Sst I restriction endonuclease site was created close to the α-factor prepro-B-chain boundary (FIG. 8). This was accomplished by oligonucleotide-directed mutagenesis (Zoller and Smith, DNA 3: 479–488, 1984) on a single-stranded pVSB template using established techniques. The mutagenic oligonucleotide used is termed ZC506 and can be seen in Table 2.

TABLE 2

| | |
|---|---|
| ZC505 | GAACCCAGGCTTGCAGCTGGCAAAGATACCCC |
| ZC506 | GGCTCCTTTTGAGCTCAGATACCCCT |
| ZC545 | GATCTCGTAGATAACGGTACGCGTCTTACAAACAGCTCTCTTGAGCT |
| ZC546 | CAAGAGAGCTGTTTGTAAGACGCGTACCGTTATCTACGA |
| ZC547 | CAAGAGATCTATCGAAGAAGCGGTACCAGCCGTTTGTAAGACGCGTGA |
| ZC548 | GATCTCACGCGTCTTACAAACGGCTGGTACCGCTTCTTCGATAGATCTCTTGAGCT |
| ZC671 | CGCGTCTTAGAAACAGCTG |
| ZC672 | GTACCAGCTGTTTCTAAGA |
| ZC675 | CAAGTGTGAAACCGTTGCTGCTGCTAGACCAGTTACCTAAT |
| ZC676 | CTAGATTAGGTAACTGGTCTAGCAGCAGCAACGGTTTCACACTTGCATG |
| ZC685 | CAAGAGATCCTTGGGTTCTTTGACCATCGCTGAA |
| ZC686 | AGCTGGTTCAGCGATGGTCAAAGAACCCAAGGATCTCTTGAGCT |
| ZC687 | CCAGCTATGATCGCTGAATGTAAGACCAGAACCGAAGTTTTCGA |
| ZC688 | GATCTCGAAAACTTCGGTTCTGGTCTTACATTCAGCGATCAT |
| ZC692 | GATCCCAAGATCCCAAGTTGACCCAACCTCTGCCAACTTC |
| ZC693 | TTGGCAGAGGTTGGGTCAACTTGGGATCTTGG |
| ZC746 | TTGATTTGGCCACCATGTGTTGAAGTTAAGAGATGTACTGGGTGT |
| ZC747 | CAGTACATCTCTTAACTTCAACACATGGTGGCCAAATCAAGAAG |
| ZC748 | TGTCAAACCTCGAGTGTTAAGTGTCAACCATCCAGAGT |
| ZC749 | GATGGTTGACACTTAACACTCGAGGTTTGACAACACC |
| ZC750 | TCACCACAGATCCGTTAAGGTTGCCAAGGTTGAATACGTTAGAAAGAAGCCAA |
| ZC751 | AGCTTTGGCTTCTTTCTAACGTATTCAACCTTGGCAACCTTAACGGATCTGTGGTGAACTCTG |
| ZC752 | AGCTTAAGGAAGTTCAAGTTAGATTGGAAGAACACTTGGAATGTGCATGCGCTACCACCTCTTTGAACCC AGACTACAGAGAATAAT |
| ZC753 | CTAGATTATTCTCTGTAGTCTGGGTTCAAAGAGGTGGTAGCGCATGCACATTCCAAGTGTTCTTCCAATC TAACTTGAACTTCCTTA |
| ZC ABA-1 | CGCTTGTGCTACCACCTCTTTGAACCCAGACTACAGAGAATAAT |
| ZC ABA-2 | CTAGATTATTCTCTGTAGTCTGGGTTCAAAGAGGTGGTAGCACAAGCGCATG |

A Pst I—Xba I fragment of pVSB (FIG. 8) was subcloned into the M13 phage vector mp19. Single-stranded template DNA was prepared from *E. coli* JM107 cultures infected with this recombinant phage and used in the following mutagenesis reaction. Five ul of M13 template DNA (0.5 picomole) were combined with 2 ul of oligonucleotide ZC506 (1.8 pmole) plus 2.5 ul of water and 1.5 ul of 10X annealing buffer A (0.2M Tris-HCl, 0.0M $MgCl_2$, 0.01M DTT pH 7.5; Zoller and Smith, *DNA* 3: 47914 488, 1984). This mixture was annealed by heating to 70° C. for 5 minutes, cooled slowly to room temperature and then placed on ice. To this cold annealing mixture was added 1.5 ul of 10X elongation buffer B (0.2M Tris-HCl, 0.1M $MgCl_2$, 0.1M DTT pH 7.5, Zoller and Smith, ibid.), 6 ul of deoxynucleotide triphosphates (2.5 mM each dNTP), 1 ul of $T_4$ DNA ligase, 1 ul of DNA polymerase Klenow fragment, 1 ul ATP (10 mM), and 5 ul of water. This mixture was incubated for 16 hours at 18° C. This reaction mixture was then diluted 20-fold with water, and 2 ul of the dilute mixture was used to transform *E. coli* JM107 cells. The resulting phage plaques were transferred to nitrocellulose discs by the procedure of Benton and Davis (*Science* 196: 180, 1977) and screened with $^{32}$P-labeled ZC506 which was labeled with $T_4$ polynucleotide kinase under standard conditions. The hybridization of the $^{32}$P-ZC506 to the filters was performed at 37° C. in 6X SSC (0.9M NaCl, 0.09M Na Citrate, pH 7.2), 100 ug/ml carrier DNA, 0.05% sodium pyrophosphate. Following hybridization, the filters were washed at 54° C. in 6X SSC, 0.1% SDS. Phage plaques giving strong autoradiographic signals were picked and RF DNA made and analyzed for the presence of a new Sst I restriction endonuclease site. The sequence around the Sst I site was also confirmed by DNA sequence analysis. The Pst I-Xba I subclone now containing an Sst I site was ligated back into Pst I-Xba I digested pVSB and the resulting plasmid termed pSB1. Plasmid pSB1 encodes two amino acid changes (Leu to Glu and Asp to Leu) in the alpha-factor leader just upstream of the Lys-Arg. The resulting junction sequence is: α-factor . . . Glu Leu Lys Arg Ser. . . B-chain. The B-chain coding sequences of pSB1 are thus flanked by an Sst I site at the 5′ end and an Xba site at the 3′ end.

EXAMPLE VII

Construction of Variants and Derivatives of the B-chain

A. Construction of a Human B-chain Expression Unit.

The B-chain construction pVSB described in Example IV above encodes the monkey B-chain amino acid sequence derived from the v-sis gene. This B-chain amino acid sequence differs from the human B-chain amino acid sequence at four positions: 6, 7, 101 and 107. These amino acid differences are largely conservative and not likely to affect the biological activity of the B-chain.

In order to express authentic human B-chain, the monkey-specific amino acids were changed to the human sequence by incorporating synthetic oligonucleotide duplexes, encoding the human amino acids into the pVSB construction. In this case, the preferred starting vector was pSB1 (described above), which has an Sst I site introduced at the α-factor-B-chain junction. The DNA sequences between this Sst I site and the Bgl II site at amino acid #24 (FIG. 9) were replaced to encode the human amino acids threonine and isoleucine at positions 6 and 7. Four oligonucleotides, ZC685, ZC686, ZC687 and ZC688 (Table 2), were designed to replace the pSB1 sequences between Sst I and Bgl II. ZC685 and ZC686 were annealed to form one duplex, and ZC687 and ZC688 were annealed to form the other. These two annealed duplexes were then ligated with Sst I-Bgl II digested pSB1 vector. The resulting plasmid was confirmed by DNA sequencing and termed pSB11.

The amino acid changes at the B-chain carboxyl end were made in a similar fashion. Plasmid pSB11 is digested with Sph I and Xba I and the sequences in this region were replaced by a synthetic DNA duplex designed to encode human amino acids threonine at position 101 and proline at position 107. Oligonucleotides ZC675 and ZC676 were annealed and ligated into Sph I-Xba I digested pSB11 under standard conditions. The construction was confirmed by DNA sequencing and termed pB12. This plasmid encodes the authentic human B-chain amino acid sequence.

Alternatively, the human B-chain amino acid sequence could be expressed by performing site-specific mutagenesis on the pVSB plasmid to change the four amino acids in question or by expressing a human B-chain cDNA sequence.

B. Monomer-Size B-chain Mutant.

Biologically active PDGF, as it is isolated from platelets or transformed cells in culture, is a disulfide bonded dimer. Chemical reduction of this dimer molecule destroys its biological activity. Surprisingly, it has been found that changing B-chain cysteine residues which are involved in interchain disulfide bonds to other amino acids or changing amino acids near these cysteine residues allows the B-chain polypeptide to fold properly but not permit interchain disulphide bonds to occur. This results in a monomer B-chain folded in a confirmation which permits binding to the PDGF cell surface receptor. Changing B-chain amino acid lysine 98 to a leucine has resulted in a molecule which is active as a monomer. This molecule is made as follows.

Plasmid pVSB (FIG. 8) is digested with Sph I and Xba I, and the DNA sequences between these restriction sites are replaced with a synthetic oligonucleotide duplex. The duplex is formed by annealing oligonucleotides analogous to ZC299 and ZC300, but containing a leucine codon at position 98 instead of a lysine codon. All the other codons in this region are preserved and encode B-chain amino acid sequence. The annealed duplex has a 5' Sph I cohesive end and a 3' Xba I cohesive end and is ligated into the Sph I-Xba I digested pVSB. This B-chain mutant is termed pSB6.

When this construction is cloned into the pMpOT2 plasmid (then termed pSB6m) and transformed into yeast, it produces mitogenically active material. Furthermore, when the expressed mitogenic material is fractionated on a polyacrylamide gel and subsequently eluted from slices of the gel, mitogenically active material is found in the monomer size range of the gel. This demonstrates that it is possible to produce a biologically active PDGF monomer by altering cysteine residues or the environment around them. Mutagenesis of other cysteine residues in the molecule may therefore be expected to lead to a similar result.

C. Truncated Amino Terminal B-chain Mutant.

During biosynthesis of the B-chain in the yeast expression system, the α-factor prepro polypeptide is removed from the B-chain by proteolytic processing at the basic dipeptide, Lys-Arg. Another basic dipeptide Arg-Arg occurs 27 amino acids downstream in the B-chain (FIG. 9). It was of interest to know if the yeast processing machinery would process the B-chain at this internal site and still yield an active protein. In order to drive the proteolytic processing to occur at the internal Arg-Arg site, the Lys-Arg at the α-factor-B-chain boundary was removed by oligonucleotide directed mutagenesis.

The mutagenesis was performed essentially as described for the construction of pSB1 above. The Pst I—Xba I fragment of pVSB (FIG. 8) was subcloned into the M13 phage vector mp19 and single-stranded template DNA prepared. In this case, the mutagenic oligonucleotide used, ZC505 (Table 2), was designed to change the -factor Lys-Arg residues to Gly-Leu and to introduce a new Pvu II restriction site. The mutagenesis reactions were carried out as described above for pSB1 and the resulting mutants screened for the new Pvu II site and then confirmed by DNA sequence analysis. The mutagenized Pst I-Xba I fragment was subcloned back into the B-chain expression unit (pVSB) and the new plasmid termed pSB3.

EXAMPLE VIII

Construction of Variants and Derivatives of the A-chain

A. Synthesis of the A-chain Amino Terminus and Construction of A-B Hybrid Fusions.

The A-chain coding sequences were inserted into the pSB1 vector as short synthetic oligonucleotide duplexes designed to encode known A-chain amino acid sequence (Johnson et al., *EMBO J.* 3: 921–928, 1984). ZC545 and ZC546 (Table 2) were annealed, creating a short duplex DNA fragment with a 5' Sst I cohesive end, a unique Mlu I restriction site, and a 3' Bgl II cohesive end. This duplex was cloned into Sst I and Bgl II digested pSB1. One ul of pSB1 vector (0.15 pmol) was combined with 1 ul of ZC546 (~1.6 pmole) and 0.6 ul of ZC545 (~1.5 pmole), plus 0.25 ul of 0.3M NaCl (final NaCl concentration in the annealing reaction is 30 mM) and the mixture was heated to 60° C. for five minutes. After heating, the mixture was brought to room temperature and then placed on ice. Then 0.5 ul of 10X ligase buffer (0.5M Tris-HCl, 0.1M MgCl$_{12}$, 2M DTT, 0.01M ATP, pH 7.8), 0.1 ul of T$_4$ DNA ligase (New England Biolabs) and 2.5 ul of water were added and this ligation mixture was diluted and used to transform *E. coli* HB101 cells. Ampicillin-resistant, plasmid-bearing colonies were picked, grown up and plasmid DNA isolated by the "miniprep" method of Ish-Horowicz and Burke (Nuc. Acid Res. 9: 2989–2998, 1981). The plasmids were analyzed for the presence of an Sst I-Bgl II insert and a new Mlu I restriction site and confirmed by DNA sequence analysis. The ZC545-546 duplex encoded A-chain amino acids alanine 8 through tryosine 17 (FIG. 9) and the resulting plasmid was termed pA1.

ZC547 and ZC548 (Table 2) were annealed to create a second short Sst I—Bgl II fragment encoding A-chain amino acids serine 1 through arginine 13 (FIG. 9) and also containing an Mlu I restriction site. The ZC547-548 duplex was separately cloned into Sst I and Bgl II digested pSB1. One ul of pSB1 (1.5 pmole) digested with Sst I and Bgl II was combined with 2 ul of ZC547 (1 pmole) and 2 ul of ZC548 (1 pmole) plus 0.25 ul of 0.3M NaCl and the mixture was heated to 50° C. for five minutes. After heating, this annealing mixture was brought to room temperature and then placed on ice. Then 0.6 ul of 10X ligase buffer and 0.1 ul of $T_4$ DNA ligase (New England Biolabs) were added and the reaction was incubated overnight at 12° C. An aliquot of this ligation reaction was diluted and used to transform E. coli HB101 cells and the resulting plasmids were screened and analyzed as described above for pA1. In this case, the resulting plasmid was termed pA2.

The overlapping pA1 and pA2 A-chain coding regions were joined at the unique Mlu I restriction site using conventional techniques. Plasmid pA2 was digested with Mlu I and BAM HI and the ~1.4 kb vector (pUC containing) fragment was isolated by agarose gel electrophoresis and extracted from the agarose with CTAB (Langridge et al., Anal. Biochem. 103: 264-271, 1980). Plasmid pA1 was also digested with Mlu I and Bam HI and the ~800 base pair fragment, encoding A-chain amino acids 13 through 17 fused to B-chain amino acids 24 through 109 followed by the TPI terminator, was isolated and extracted as above. Equimolar amounts of these two fragments were ligated under standard conditions and an aliquot used to transform E. coli HB101 cells. Plasmids obtained from ampicillin-resistant colonies were analyzed by restriction enzyme digestion for the correct fragments and confirmed by DNA sequencing. The resulting plasmid termed pA3 thus encoded a hybrid protein beginning with A-chain amino acids 1 through 17 followed in frame by B-chain amino acids 24 through 109. The Cla I—Bam HI fragment of pA3 containing the entire expression unit was cloned into pMPOT2 and the resulting plasmid pA3m was transformed into yeast.

Further addition of A-chain amino acids to the A-B hybrid was accomplished in a similar fashion. Plasmid pA3 was digested first with Asp718, which cuts the plasmid once in the A-chain sequence at proline codon 7, and with Bam HI, and the hybrid amino acid coding fragment subcloned into pUC118. This subclone was termed pA3N and was subsequently digested with Bgl II and Bst XI. Bgl II cuts at the boundary of the A- and B-chain sequences in the hybrid and Bst XI cuts approximately 40 base pairs downstream in the B-chain. The vector fragment (pUC containing) from this digest was isolated by agarose gel electrophoresis and extracted with CTAB. One picomole each of oligonucleotides ZC692 and ZC693 (Table 2) was annealed to form a short DNA duplex with a 5' Bgl II end and a 3' Bst XI end. This duplex encoded A-chain glutamic acid 18 through phenylanine 31 and was ligated with 0.1 picomole of Bgl II-Bst XI digested pA3N. The ligation was performed overnight and the ligated products transformed into E. coli MV1193 cells. The resulting plasmid termed pA6N now has extended the A-chain amino acid sequence to the Bst XI site at amino acid A31 followed by B-chain amino acids B38 through B109.

Plasmid pA6N was then digested with Asp718 and Bam HI and the A-B hybrid fragment cloned back into Asp718-Bam HI digested pA3m. This new A-B hybrid plasmid is termed pA6m and encodes A-chain amino acid sequence up to amino acid 40 because the Bst XI site lies at the start of a region of high homology between A- and B-chains.

B. Construction of A-B-A Hybrid Fusions.

Since the A- and B-chains of PDGF are so homologous in structure and function, there are likely to be several biologically active hybrid molecules which can be made between the two. A number of examples containing amino terminal A-chain sequence followed by B-chain amino acids are described above. Another example of this concept would be to construct a hybrid protein which contained A-chain amino acid sequence at the amino and carboxyl termini and B-chain sequence in the middle.

A preferred embodiment would use plasmid pA6, which encodes the hybrid protein A1-17, B24-109, and to exchange A-chain for B-chain amino acid sequence at its carboxyl end. In this case, the B-chain coding region is digested with the restriction endonuclease Sph I, which cuts in B-chain codons 96 and 97 (FIG. 9). The plasmid pA6 is cut again with Xba I, which cuts immediately 3' of the translation termination codon. This sequence is then replaced with two oligonucleotides which, when annealed, form a duplex with 5' and 3' Sph I and Xba I cohesive ends, respectively, and contain A-chain codons (FIG. 9). The two oligonucleotides, ZC ABA-1 and ZC ABA-2, are shown in Table 2. These two oligonucleotides are annealed by heating to 65° C. and slow cooling as described above. The annealed duplex is then ligated into Sph I-Xba I digested pA6 plasmid which has been isolated by agarose gel electrophoresis. The ligated product is transformed into *E. coli* MV1193 cells and transformed colonies obtained on ampicillin plates. In this case, no new restriction sites are introduced by the new A-chain duplex, so the construction is confirmed by DNA sequence analysis.

C. Construction of an A-chain Cysteine Mutant.

As can be seen from FIG. 9, both the A- and B-chains of PDGF contain eight cysteine residues which are capable of forming disulphide bonds. It can also be seen from FIG. 9 that these cysteine residues are in analogous positions in the two polypeptides and hence may participate in similar disulfide arrangements in and between the two chains and even between two different chains (A and B). It has been known for several years that chemical reduction of the disulfide-bonded PDGF dimer to monomers destroys its biological activity. It is of interest to know which of the cysteine residues in question are involved in disulfide bonds of both the intra- and intermolecular type. It is very likely that the role of each cysteine will be analogous in both A- and B-chains.

The first cysteine residue in the A-chain occurs at position #10, which is analogous to #16 in the B-chain (FIG. 9). The A-B hybrid pA3 (described above) encodes A-chain amino acids 1-17, followed by B-chain. The synthetic strategy leading to construction of pA3 incorporated unique restriction sites flanking the cysteine at residue A10. An Asp718 and an Mlu I restriction site were placed 5' and 3', respectively, to the A10 cysteine codon approximately 20 base pairs apart. Two oligonucleotides (ZC671 and ZC672, Table 2) were synthesized and annealed to form a short DNA duplex with a 5' Asp718 cohesive end and a 3' Mlu I cohesive end. This duplex encodes a serine residue in place of cysteine A10. Plasmid pA3 was digested with Asp718 and Mlu I and the large vector (pUC containing) fragment isolated by agarose gel electrophoresis. Equimolar amounts of the vector and the ZC671-672 duplex were ligated under standard conditions as described above and then transformed into *E. coli* MV1193 cells. Plasmid (miniprep) DNA was prepared from the resulting transformants and screened for a new Pvu II site present in the ZC671-672 duplex. The duplex region of the plasmid is then confirmed by DNA sequence analysis. The resulting plasmid, termed pA5, encodes an A-B hybrid protein with A-chain amino acids 1-17 at the amino terminus, but residue 10 is a serine instead of a cysteine. The remaining amino acids of the pA5 hybrid are the normal B-chain residues (Glu 24 through Thr 109).

D. Complete Synthesis of the A-chain Gene.

The remainder of the A-chain gene was synthesized with oligonucleotides in a fashion very similar to that described above. Many strategies could be designed to accomplish this task. One such strategy is described below. The oligonucleotides used in this strategy are shown in Table 2 and their design reflects optimal codon usage for *Saccharomyces cerevisiae*. In this strategy, the remainder of the A-chain gene was synthesized with unique restriction sites introduced in order to facilitate subcloning and sequencing the synthetic oligonucleotide sequences. All the oligonucleotides were synthesized on an Applied Biosystems 380-A DNA synthesizer. Oligonucleotides ZC752 and ZC753, each 87mers, were annealed and subcloned as a Hind III—Xba I fragment encoding A-chain amino acids 77-104. ZC752 and ZC753 (1.25 picomole each) were annealed in 5 ul of 40 mM NaCl by heating to 65° C. for 15 minutes and then allowing the mixture to come to room temperature and putting on ice. One tenth of this annealed duplex (0.0125 picomole) was ligated into both pUCl18 (0.07 pmole) and M13 mp18 (0.02 picomole) which were previously digested with Hind III and Xba I. The ligated mixtures were used to transform the appropriate *E. coli* host strain (JM107 in the case of M13 mp18 and MV1193 in the case of pUCl18) and the resulting plasmid or RF DNAs analyzed by restriction endonuclease digestion and DNA sequencing.

The oligonucleotides ZC746+747, 748+749, and 750+751 were designed to form short duplexes with cohesive ends which when joined would constitute the sequence between the Bst XI site at A31 and the Hind III site at A77. The oligonucleotides were phosphorylated with $^{32}$P and T$_4$ polynucleotide kinase under standard conditions. The pairs ZC746+ZC747, ZC748+ZC749, and ZC750+ZC751 were each annealed by combining 2.5 pmole of each oligonucleotide in 5 ul of 40 mM NaCl, heating to 65° C. for 15 minutes, allowing to come to room temperature, and putting on ice. The three annealing mixtures were combined (now 15 ul) and ligated in a final volume of 20 ul. The ligated products were electrophoresed in a 4% NuSieve agarose gel (FMC Corporation) in TBE buffer (90 mM Tris, 90 mM boric acid, 2 mM disodium EDTA) followed by autoradiography. The ~140 base pair fragment corresponding to the three correctly ligated duplexes was cut out of the gel and extracted with CTAB. This fragment, together with the previously cloned Hind III-Xba I fragment, was ligated into the Bst XI-Xba I digested pA6N vector. The resulting plasmid was termed pA6N+. Plasmid pA6N+ was then digested with Asp718 and Xba I and the A-chain coding fragment cloned back into pA3. This plasmid pA7 encodes the entire mature A-chain.

For purposes of yeast expression, a preferred embodiment would employ oligonucleotides ZC748 and ZC749. These encode a glutamine at position A-48 instead of an asparagine. This change destroys the N-linked glycosylation site which can be aberrantly glycosylated in yeast. Oligonucleotides designed to preserve the N-linked glycosylation site could also be used.

The strategy employing total gene synthesis described above is desirable because the amino acid sequence of the A-chain is known and the codon usage can be optimized for yeast. Alternatively, an A-chain cDNA seqence could be expressed in yeast or other eukaryotic cells, provided the cDNA was appropriately incorporated into a suitable expression vector. An A-chain cDNA could be obtained from a variety of mammalian cell lines by conventional techniques (Betsholtz, C. et al., *Nature* 320, 695-699, 1986.)

EXAMPLE IX

Insertion of Expression Unit Constructions into pMPOT2

Each of the molecules constructed in Examples VI--VIII above was introduced back into the basic expression unit pVSB or pSB1 if the Sst I site was employed. Then each of them was ultimately cloned into the yeast plasmid $pMPOT_2$ (Example IV). In each case, this was done by removing the expression unit as a single fragment from pVSB or pSB1 by Cla I-Bam HI digestion. The Cla I—Bam HI fragment of each was isolated by agarose gel electrophoresis and cloned into $pMPOT_2$ which had been digested with Cla I and Bam HI. The names of the resulting plasmids are then amended with a lower case "m," e.g., pA2 becomes pA2m.

Each of the mPOT constructions was then transformed into the yeast strain E18-#9 (Example VI).

EXAMPLE X

A-B Heterodimer Expression Construction

PDGF is a disulfide-bonded dimer, and as isolated from platelets, is composed of two amino acid chains, an A-chain and a B-chain. It is presumed that this material is in the form of an A-B heterodimer. There are now a number of examples of PDGF homodimers composed of either A- or B-chain (Kelly et al., *EMBO J.* 4: 3399-3405 1985; Stroobant and Waterfield, *EMBO J.* 3: 2963, 1984; and Heldin et al., *Nature* 319: 511, 1986). While platelet PDGF is still thought to be a heterodimer, these data raise the possibility that it may actually be a mixture of A-A and B-B homodimers.

Having expressed biologically active A and B forms of PDGF in the yeast expression system, it is possible to introduce both an A- and a B-chain expression unit into the same yeast cell and to identify A-B heterodimers among the biologically active products. This can be done by introducing the respective expression units into the yeast cell on different plasmids, possibly with different selectable markers. Using this strategy, it may be difficult to control the relative copy numbers of the two plasmids and this may result in disproportionate amounts of the A- and B-chain polypeptides in the cell. A preferred strategy would be to put both the A-chain and B-chain expression units on the same plasmid. In this way, their copy numbers would always be equal.

There are numerous ways to incorporate both expression units into the same plasmid. One simple way would be as follows. Remove the B-chain expression unit from plasmid pVSB (FIG. 8) by complete digestion with Bam HI followed by partial digestion with Bgl II. The fragment corresponding to the expression unit (TPI promoter-MF α-1-B-chain-terminator) is isolated by agarose gel electrophoresis and subcloned into the Bam HI site of pUCl8. The orientation of the insert in the resulting subclones is established by conventional restriction enzyme digestions. A subclone in which the Bgl II end of the insert is adjacent to the Sal I site in the polylinker is chosen for the next step. This subclone is digested with Sal I and Bam HI and the insert fragment isolated. This B-chain fragment is then ligated into plasmid pA7m, which had been digested with Sal I and Bam HI. The resulting plasmid pABm contains both the A- and the B-chain expression units oriented tail to tail. This plasmid is then transformed into yeast strain E18-#9.

EXAMPLE XI

Biological Activity Assays

A. Radioreceptor Assay (RRA) for PDGF.

The radioreceptor assay for PDGF (Bowen-Pope and Ross, *J. Biol. Chem.* 257: 5161, 1982) is a specific and sensitive (0.2–2 ng/ml PDGF) method for detecting biologically active PDGF-like material in yeast. In this assay, PDGF-like material is tested for its ability to compete with purified, radio-labeled $^{125}$I PDGF for binding sites on cell surface PDGF receptors. Results are interpreted by comparison to a standard curve generated with purified, unlabeled PDGF. Comparison of results obtained with other assay methods (e.g., ELISA) provides an indication of the strength of the receptor/ligand interaction in addition to quantitation of the material bound. The assay is conducted as follows: Subconfluent monolayers of diploid human fibroblasts are prepared by plating $1.5 \times 10^4$ cells per 2 cm$^2$ culture well in Costar 24 well cluster trays in Dulbecco's Modified Eagles Medium (DMEM) supplemented with 1% human plasma-derived serum (PDS). Cultures are set on an ice tray and rinsed once with ice-cold binding rinse (Ham's medium F-12 buffered at pH 7.4 with 25 mM HEPES and supplemented with 0.25% BSA). One ml/well of test substance in binding medium is added and the cultures incubated in a refrigerated room on an oscillating platform for 3–4 hours. The trays are then placed on ice, aspirated, rinsed once with cold binding rinse and incubated for one hour as above with 1 ml/well binding medium containing 0.5 ng/ml $^{125}$I-PDGF. Labeling is terminated with four rinses of binding rinse and cell-associated $^{125}$I-PDGF determined by extraction with solubilization buffer. Standard curves are obtained using 0, 0.05, 0.1, 0.2, 0.4, and 0.8 ng/ml purified pDGF and test samples compared to these values.

Figure 10:
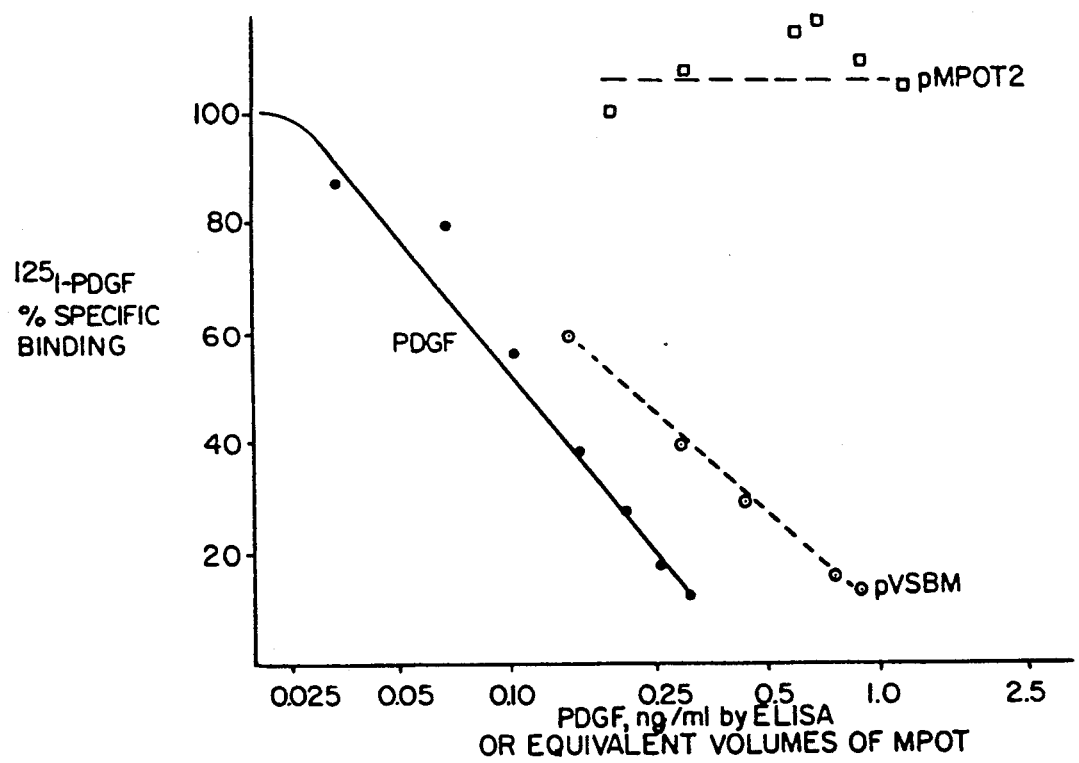
FIG. 10 is a dose response curve of PDGF receptor binding by media concentrates from yeast transformants containing plasmids pVSBm and pMPOT2 compared to authentic PDGF.

PDGF receptor binding by CM-Sephadex media concentrates from yeast transformants containing plasmids pVSBm and pMPOT$_2$ was compared to receptor binding by authentic PDGF. After concentration by binding to and elution from CM-Sephadex, the pVSBm concentrate was normalized to PDGF equivalents in an ELISA using polyclonal goat antibody to PDGF. The RRA results were interpreted by comparison to a standard curve generated with purified, unlabeled PDGF, as shown in FIG. 10. Media from cultures transformed with the pVSBm constructions are shown to compete with $^{125}$I-PDGF for binding to the PDGF receptor. Media from yeast cells transformed with pMPOT$_2$ do not compete with radio-labeled PDGF for receptor binding.

B. Mitogenesis Assay.

The ability of PDGF to stimulate DNA synthesis and cell growth in culture was the basis for its definition and discovery. $^3$H-Thymidine incorporation into DNA of cultured cells responsive to PDGF (Raines and Ross, *Meth. in Enzomology* 109: in press) is a preferred method for demonstrating the biological activity of PDGF-like molecules produced in yeast.

Straight spent media test samples or concentrates of spent media or test samples in 10 mM acetic acid (up to 100 ul/well) are added to quiescent cultures of mouse 3T$_3$ cells in 2 cm$^2$ Costar 24-well culture dishes ($2-3 \times 10^8$ cells/well in 1 ml). Quiescent test cultures can be obtained by plating the cells in 10% serum and allowing them to deplete the medium, 4–5 days. The test samples are removed from the wells at 20 hours and replaced with 0.5 ml of fresh medium per well containing 2 uCi/ml [$^3$H]-Thymidine and 5% (v/v) calf serum. After an additional two-hour incubation at 37° C. the cells are harvested by: aspirating off the medium, washing the wells twice each with 1 ml of ice-cold 5% TCA; solubilizing TCA-insoluble material in 0.8 ml 0.25N NaOH with mixing; and counting 0.6 ml of this solution in 5 ml Aquasol in a liquid scintillation counter. Fold stimulation cover control wells (100 ul of 10 mM acetic acid alone) is determined (normally 30–50 fold maximal stimulation) and compared to a standard curve obtained using purified PDGF preparations.

TABLE 3

| | PDGF mitogenic activity (ng/ml) | |
|---|---|---|
| Constructions | Media Concentrates | Straight Media |
| pVSB | 10,000 ng/ml | ~160 ng/ml |
| pSB3 | 1,700 ng/ml | |
| pSB6 | 158 ng/ml | |
| pA5 | 1,025 ng/ml | |
| pA3 | | 50 ng/ml |
| pA7 | | ~150 ng/ml |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A mitogenic protein produced by a method comprising:
   (a) introducing into a eucaryotic host cell a DNA construct capable of directing the expression and secretion of biologically active PDGF analogs in eucaryotic cells, said DNA construct containing a transcriptional promoter followed downstream by a DNA sequence that encodes the B-chain of a primate PDGF; and
   (b) isolating from the host cell a mitogenic protein, which is a PDGF BB Romodimer, expressed from said DNA construct.

* * * * *

UNITED STATES PATENT AND TRADEMARK OFFICE
CERTIFICATE OF CORRECTION

PATENT NO. : 5,187,263

DATED : February 16, 1993

INVENTOR(S) : Mark J. Murray and James D. Kelly

It is certified that error appears in the above-identified patent and that said Letters Patent is hereby corrected as shown below:

On title page, item [54] and col. 1, line 1, in the title, delete "PDGE" and substitute therefor -- PDGF --.

In column 28, claim one, line 60, please delete "Romodimer" and substitute therefor -- homodimer --.

Signed and Sealed this

Seventh Day of December, 1993

Attest:

BRUCE LEHMAN

*Attesting Officer*   *Commissioner of Patents and Trademarks*